(12) United States Patent
Henwood et al.

(10) Patent No.: US 9,795,559 B2
(45) Date of Patent: Oct. 24, 2017

(54) INTRANASAL DEXMEDETOMIDINE COMPOSITIONS AND METHODS OF USE THEREOF

(71) Applicant: RECRO PHARMA, INC., Malvern, PA (US)

(72) Inventors: Geraldine A. Henwood, Malvern, PA (US); Randall J. Mack, Paoli, PA (US); John Joseph Koleng, Jr., Austin, TX (US); Christopher T. Sharr, Malvern, PA (US); Charles Alexander Freyer, Glenside, PA (US)

(73) Assignee: Recro Pharma, Inc., Malvern, PA (US)

( * ) Notice: Subject to any disclaimer, the term of this patent is extended or adjusted under 35 U.S.C. 154(b) by 0 days.

(21) Appl. No.: 13/711,407

(22) Filed: Dec. 11, 2012

(65) Prior Publication Data

US 2013/0178465 A1 Jul. 11, 2013

Related U.S. Application Data

(60) Provisional application No. 61/569,255, filed on Dec. 11, 2011.

(51) Int. Cl.
| | | |
|---|---|---|
| A61K 9/00 | (2006.01) | |
| A61K 31/4174 | (2006.01) | |
| A61K 45/06 | (2006.01) | |
| A61K 9/08 | (2006.01) | |

(52) U.S. Cl.
CPC ............. *A61K 9/0043* (2013.01); *A61K 9/08* (2013.01); *A61K 31/4174* (2013.01); *A61K 45/06* (2013.01)

(58) Field of Classification Search
None
See application file for complete search history.

(56) References Cited

U.S. PATENT DOCUMENTS

| | | |
|---|---|---|
| 4,910,214 A | 3/1990 | Karjalainen et al. |
| 5,091,402 A | 2/1992 | Kalso et al. |
| 5,124,157 A | 6/1992 | Colley et al. |
| 5,217,718 A | 6/1993 | Colley |
| 5,438,067 A | 8/1995 | Jalonen |
| 5,485,827 A | 1/1996 | Zapol et al. |
| 5,571,840 A | 11/1996 | Mayor et al. |
| 5,713,907 A | 2/1998 | Hogendijk et al. |
| 6,313,311 B1 | 11/2001 | Karjalainen et al. |
| 6,562,855 B1 | 5/2003 | Franks |
| 6,716,867 B1 | 4/2004 | Aantaa et al. |
| 6,978,945 B2 | 12/2005 | Wong |
| 7,001,609 B1 | 2/2006 | Matson et al. |
| 2003/0022926 A1 | 1/2003 | Lavand'Homme |
| 2003/0077227 A1 | 4/2003 | Dugger |
| 2003/0124191 A1 | 7/2003 | Besse et al. |
| 2005/0281752 A1 | 12/2005 | Dugger |
| 2006/0264515 A1 | 11/2006 | DeJovin et al. |
| 2008/0004305 A1 | 1/2008 | Wermeling |
| 2008/0021074 A1 | 1/2008 | Cartt |
| 2008/0070904 A1* | 3/2008 | Jamieson ............. A61K 9/0043 514/220 |
| 2008/0131483 A1 | 6/2008 | Abdulrazik |
| 2009/0117054 A1 | 5/2009 | Crooks |
| 2011/0021426 A1 | 1/2011 | Toll et al. |
| 2011/0021588 A1 | 1/2011 | Henwood et al. |

FOREIGN PATENT DOCUMENTS

| | | |
|---|---|---|
| CN | 1049450 A | 2/1991 |
| GB | 2206880 | 1/1989 |
| JP | 2006516262 | 7/2004 |
| NZ | 234749 | 3/1992 |
| PT | 1069893 E | 1/2007 |
| RU | 2098083 | 12/1997 |
| RU | 2208582 | 7/2003 |
| RU | 2244558 C2 | 1/2005 |
| WO | 9102505 | 3/1991 |
| WO | 9221338 | 12/1992 |
| WO | 9505820 | 3/1995 |
| WO | 9712874 | 4/1997 |
| WO | 9924023 | 5/1999 |
| WO | 9949854 | 10/1999 |
| WO | 0023066 | 4/2000 |
| WO | 0076545 | 12/2000 |
| WO | 02065941 | 8/2002 |
| WO | 2006011915 | 2/2006 |
| WO | 2007093824 | 8/2007 |
| WO | 2008059190 | 5/2008 |
| WO | 2009086055 A1 | 7/2009 |
| WO | 2010132882 A2 | 11/2010 |
| WO | 2011085162 | 7/2011 |

OTHER PUBLICATIONS

Suman et al. (Pharmaceutical Research vol. 19, No. 1, Jan. 2002, pp. 1-6).*
Yuen et al. (Anesth Analg 2008;106:1715-21).*
Yuen et al. (Anesthesia, 2010 65, pp. 922-929).*
Intranasal Website at web address: intranasal.net/overview/default.htm, accessed Oct. 2016.*
U.S. Appl. No. 13/520,959, filed Dec. 3, 2012, which is a U.S. National Phase Application, Application No. PCT/US11/20462, filed Jan. 7, 2011 which claims priority to U.S. Appl. No. 61/293,440, filed Jan. 8, 2010.
U.S. Appl. No. 12/781,628, filed May 17, 2010, which claims priority to U.S. Appl. No. 60/178,730, filed May 15, 2009.
Iirola et al., "Bioavailability of dexmedetormidine after intranasal administration.," Eur J Clin Pharm (2011) 67:825-831.
Advisory Action dated Jan. 24, 2013 received in copending U.S. Appl. No. 12/781,628.

(Continued)

*Primary Examiner* — Kortney L Klinkel
*Assistant Examiner* — William Lee
(74) *Attorney, Agent, or Firm* — Stradley Ronon Stevens & Young, LLP

(57) ABSTRACT

The present invention provides intranasal formulations comprising dexmedetomidine, or a pharmaceutically acceptable salt thereof, and uses thereof.

15 Claims, 2 Drawing Sheets

(56) References Cited

OTHER PUBLICATIONS

Advisory Action dated Apr. 23, 2013 received in copending U.S. Appl. No. 12/781,628.
Dobrydnjov et al., "Intrathecal and oral clonidine as prophylaxis for postoperative alcohol withdrawal syndrome: a randomized double-blinded study," Anesth Analg (2004) 98:738-744.
Kanazi et al "Effect of low-dose dexmedetomidine or clonidine on the characteristics of bupivacaine spinal block.," Acta Anaesthesiol. Scand. (2006) 50:222-227.
Ebert et al., "The effects of increasing plasma concentrations of dexmedetomidine in humans," Anesthesiology (2000) (93):382-394.
Gomez-Vasquez et al., "Clinical analgesic efficacy and side effects of dexmedetomidine in the early postoperative period after arthroscopic knee surgery," Journal of Clinical Anesthesia (2007) 19(8):576-582.
Chrysostomou et al., "Dexmedetomidine: sedation, analgesia and beyond," Expert Opin Drug Metab Toxicol (2008) 4 (5):619-627.
Anttila et al., "Bioavailability of dexmedetomidine after extravascular doses in healthy subjects," Br J Clin Pharmacol (2003) 56:691-693.
Karaaslan et al., "Comparison of buccal and intramuscular dexmedetomidine premedication for arthroscopic knee surgery," Journal of Clinical Anesthesia (2006) 18:589-593.
Ugur et al., "Intrathecal infusion therapy with dexmedetomidine-supplemented morphine in cancer pain," Anaesthesia! Scand (2007) 51(3):388.
Official Action dated Dec. 1, 2005 from U.S. Appl. No. 10/111,628, filed Aug. 23, 2002.
Kivisto et al., "Pharmacokinetics and pharmacodynamics of transdermal dexmedetomidine," European Journal of Clinical Pharmacology (1994) 46:345-349.
Karadas et al, "Additive interaction of intraperitoneal dexmedetomidine and topical nimesulide, celecoxib, and DFU for antinociception," Pharmacology (2007) 556(1-3):62-68.
Onttonen et al., "The mechanical antihyperalgesic effect of intrathecally administered MPV-2426, a novel alpha2—adrenoceptor agonist, in a rat model of postoperative pain," Aesthesiology (2000) 92(6):1740-1745.
Eisenach et al., "Antinociceptive and hemodynamic effects of a novel alpha2-adrenergic agonist, MPV-2426, in sheep," Anesthesiology (1999) 91:1425-1436.
Official Action dated Oct. 28, 2010 from U.S. Appl. No. 11/641,953, filed Dec. 20, 2006.
Official Action dated Apr. 8, 2005 from U.S. Appl. No. 10/111,628, filed Aug. 23, 2002.
Official Action dated Aug. 25, 2004 from U.S. Appl. No. 10/111,628, filed Aug. 23, 2002.
Cohen et al., "Intranasal Dexmedetomidine for Sedation during CT Scanning," Amer. Society of Anesth., Annual Meeting Abstracts (2008) A998.
Angst et al., "Comparative analgesic and mental effects of increasing plasma concentrations of dexmedetornidine and alfentanil in humans," Anesthesiology (2001) 101(3):744-752.
Hall et al., "Sedative, amnestic, and analgesic properties of small-dose dexmedetomidine infusions," Anesth Analg (2000) 90(3):699-705.
Final Office Action dated Oct. 12, 2012 received in copending U.S. Appl. No. 12/781,628.
Non-Final Office Action dated Apr. 26, 2012 received in copending U.S. Appl. No. 12/781,628.
Panzer et al., "Pharmacology of sedative-analgesic agents: dexmedetomidine, remifentanil, ketamine, volatile anesthetics, and the role of peripheral mu antagonists," Crit Care Clin 2009 25(3):451-469.
Abramov et al., "The Role of Dexmedetomidine (Precedex®) in the Sedation of Critically Ill Patients," P&T (2005) 30 (3):158-161.
Dyck et al., "The pharmacokinetics and hemodynamic effects of intravenous and intramuscular dexmedetomidine hydrochloride in adult human volunteers," Anesthesiology (1993) 78(5):813-820.
Martinez et al., "[Analysis of oxidative stress in exhaled breath condensate from patients with severe pulmonary infections]." Arch Bronconeumol (2006) 51(3):113-119.
Siegel et al., "Cancer treatment and survivorship statistics, 2012," (2012) 62(4):200-241.
Zhang "Antihyperalgesic effect of systemic dexmedetomidine and gabapentin in a rat model of monoarthritis," Brain (2009) Research 1264:57-66.
Wagner et al., "Developmental time and size-related traits in *Drosophila buzzatii* along an altitudinal gradient from Argentina," (2006) 25(2):77-83.
Franken et al., "Evaluation of analgesic and sedative effects of continuous infusion of dexmedetomidine by measuring somatosensory- and auditory-evoked potentials in the rat," (2008) 35(5):424-431.
Yuen et al., "A double-blind, crossover assessment of the sedative and analgesic effects of intranasal dexmedetomidine," (2007) 105(2):374-380.
Poree et al., "The analgesic potency of dexmedetomidine is enhanced after nerve injury: a possible role for peripheral alpha2-adrenoceptors," (1998) 87(4):941-948.
Guneli e al., "Analysis of the antinociceptive effect of systemic administration of tramadol and dexmedetomidine combination on rat models of acute and neuropathic pain," (2007) 88(1):9-17.
Sowers et al., "Diabetes, hypertension, and cardiovascular disease: an update," (2001) 37:1053-1059.
Pinto dos Santos, "[Dexmedetomidine for neurocognitive testing in awake craniotomy: case report]," (2006) 56:(4):402-401).
Office Action dated Oct. 31, 2013 received in copending U.S. Appl. No. 13/520,959.
Rossi et al., "New modalities and paradigms for sedation: 'new sedation agents,'" (2009) Techniques in Gastrointestinal Endoscopy (11):171-176.
Final Office Action dated May 13, 2014 received in copending U.S. Appl. No. 13/520,959.
Berge et al., "Pharmaceutical Salts," (1977) J Pharm Sci 66:1-19.
New general statement of pharmaceutics (revised the 3rd edition), Dec. 25, 1980, p. 84.
T. Kimura, "New Administration Routes for Drugs (1), Absorption of Drugs from the Oral Mucosa", 1988, 4(16); 49-53.

* cited by examiner

INTRANASAL DEXMEDETOMIDINE COMPOSITIONS AND METHODS OF USE THEREOF

FIELD OF THE INVENTION

The present invention is directed, in part, to intranasal formulations of dexmedetomidine, or a pharmaceutically acceptable salt thereof, that are analgesic but without significant sedation, as well as methods of use thereof.

BACKGROUND

Dexmedetomidine, 5-[(1S)-1-(2,3-dimethylphenyl)ethyl]-1H-imidazole, is a non-narcotic α2-adrenoceptor agonist with sedative and analgesic properties. Currently, dexmedetomidine is only commercially available as an injectable formulation indicated for sedation of initially intubated and mechanically ventilated patients during treatment in an intensive care setting and sedation of non-intubated patients prior to and/or during surgical and other procedures, and it must be administered intravenously by an experienced and licensed health care professional. Although dexmedetomidine has analgesic properties, an intranasal formulation useful as an analgesic without sedation, however, is not commercially available. Moreover, for a variety of reasons, the commercially available injectable formulation is not suitable for use as an analgesic that can be self-administered. A continuing and unmet need exists for a dexmedetomidine-based analgesic medicine that, for example, may be self-administered by the patient intranasally to produce analgesia (or otherwise treat or prevent pain) without significant sedation.

SUMMARY OF THE INVENTION

Figure 1:
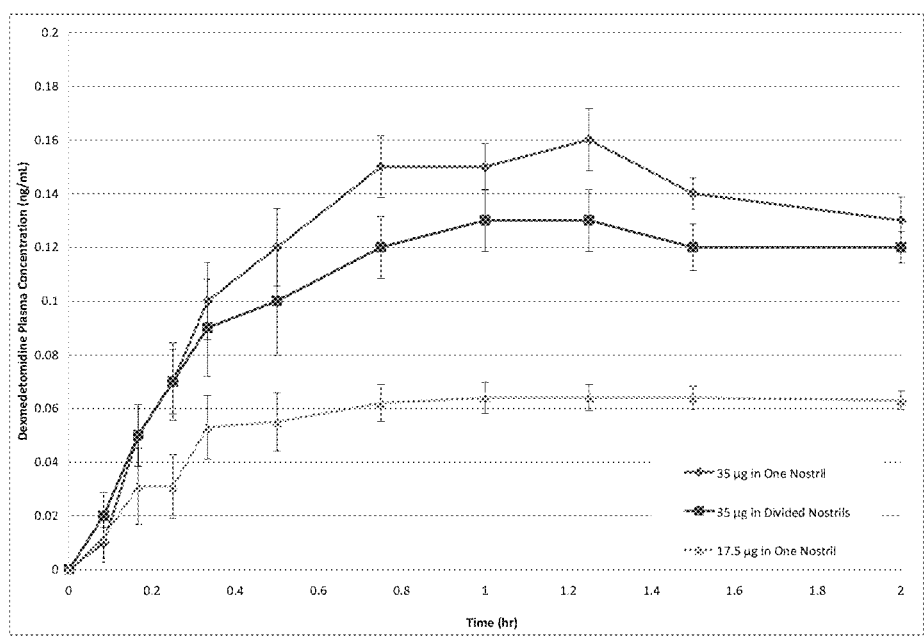
FIG. 1 shows intranasal dexmedetomidine pharmacokinetics for some embodiments.

The present invention provides methods of treating or preventing pain without significant sedation in a mammal comprising intranasally administering an intranasally effective amount of dexmedetomidine, or a pharmaceutically acceptable salt thereof, to the mammal whereby the intranasally effective amount of dexmedetomidine, or pharmaceutically acceptable salt thereof, produces a $C_{plasma}$ of about 0.1 ng/ml within about 15 minutes to about 20 minutes of administration and has an analgesic effect without significant sedation.

The present invention also provides methods of treating or preventing pain without significant sedation in an adult human comprising intranasally administering an intranasally effective amount of dexmedetomidine, or a pharmaceutically acceptable salt thereof, to the adult human whereby the intranasally effective amount of dexmedetomidine, or pharmaceutically acceptable salt thereof, does not produce significant sedation in the adult within a period of time of about two hours after administration and has an analgesic effect within the period of time.

The present invention also provides methods of treating or preventing pain without significant sedation in a mammal comprising intranasally administering dexmedetomidine, or a pharmaceutically acceptable salt thereof, to a single nostril of the mammal, particularly a human.

The present invention also provides methods of treating or preventing pain without significant sedation in a mammal comprising intranasally spraying in the mammal a pharmaceutical composition comprising dexmedetomidine, or a pharmaceutically acceptable salt thereof, wherein the spray comprises droplets which have a Dv90 of less than about 150 µm.

The present invention also provides metered dose devices comprising a pharmaceutical composition comprising dexmedetomidine, or a pharmaceutically acceptable salt thereof, wherein the metered dose device delivers a metered dose spray of the pharmaceutical composition intranasally that is analgesic in a mammal without significant sedation.

DESCRIPTION OF EMBODIMENTS

Unless defined otherwise, all technical and scientific terms have the same meaning as is commonly understood by one of ordinary skill in the art to which the embodiments disclosed belongs.

As used herein, the terms "a" or "an" means that "at least one" or "one or more" unless the context clearly indicates otherwise.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

As used herein, the term "analgesia" refers to the alleviation (partial or complete) or elimination of the sensation of pain.

As used herein, the term "carrier" means a diluent, adjuvant, or excipient with which a compound is administered. Pharmaceutical carriers can be liquids, such as water and oils, including those of petroleum, animal, vegetable or synthetic origin, such as peanut oil, soybean oil, mineral oil, sesame oil and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used.

As used herein, the term, "compound" means all stereoisomers, tautomers, and isotopes of the compounds, or pharmaceutically acceptable salts thereof, including any and all metabolites described herein.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps.

As used herein, the term "contacting" means bringing together of two elements in an in vitro system or an in vivo system. For example, "contacting" a compound or composition described herein with an individual or patient or cell includes the administration of the compound to an individual or patient, such as a human.

As used herein, the term "Dv90" means the value which represents the particle size below which 90% of the volume of a plurality of droplets exist (e.g., such as in a spray mist; in contrast to a nasal drop comprising one or two drops).

As used herein, the term "individual" or "patient," used interchangeably, means any animal, including mammals, such as mice, rats, other rodents, rabbits, dogs, cats, swine, cattle, sheep, horses, or primates, such as humans.

As used herein, the phrase "in need thereof" means that the animal or mammal has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent. For example, a mammal or animal may be in need of treatment or prevention of pain without sedation or without significant sedation.

As used herein, the phrase "metered dose device" refers to a device that provides a specified dose.

As used herein, the phrase "X to Y" means any number between X and Y and includes the endpoints. For example, the phrase "1 to 5" means 1, 2, 3, 4, or 5.

As used herein, "pain" refers to a wide range of clinical manifestations, and it has a broad meaning. Pain perception is highly subjective, and different individuals experience pain in different ways and with greatly different intensities. The International Association for the Study of Pain defines pain as "an unpleasant sensory and emotional experience associated with actual or potential tissue damage, or described in terms of such damage." More simply stated, pain includes any sensory experience that causes suffering and is associated with an unpleasant awareness of one's own body. Non-limiting types and causes of pain include neuralgia, myalgia, hyperalgesia, hyperpathia, neuritis, and neuropathy. Pain is often a symptom of an underlying physiological abnormality, such as cancer or arthritis. Some types of pain have no clearly identified causes, such as migraine headache pain. Pain may also be caused by physical trauma, such as burns or surgery. Viral infections, such as Herpes zoster (chicken pox and shingles), can also cause pain. Withdrawal from chemical dependence on alcohol or drugs of abuse is also often associated with pain symptoms. Accordingly, "pain" is understood herein to have a very broad meaning.

As used herein, the phrase "pharmaceutically acceptable" means those compounds, materials, compositions, and/or dosage forms which are, within the scope of sound medical judgment, suitable for use in contact with tissues of humans and animals. In some embodiments, "pharmaceutically acceptable" means approved by a regulatory agency of the Federal or a state government or listed in the U.S. Pharmacopeia or other generally recognized pharmacopeia for use in animals, and more particularly in humans.

As used herein, the phrase "pharmaceutically acceptable salt(s)," includes, but is not limited to, salts of acidic or basic groups. Compounds that are basic in nature are capable of forming a wide variety of salts with various inorganic and organic acids. Acids that may be used to prepare pharmaceutically acceptable acid addition salts of such basic compounds are those that form non-toxic acid addition salts, i.e., salts containing pharmacologically acceptable anions including, but not limited to, sulfuric, thiosulfuric, citric, maleic, acetic, oxalic, hydrochloride, hydrobromide, hydroiodide, nitrate, sulfate, bisulfate, bisulfate, phosphate, acid phosphate, isonicotinate, borate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, bicarbonate, malonate, mesylate, esylate, napsydisylate, tosylate, besylate, orthophoshate, trifluoroacetate, and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include, but are not limited to, alkali metal or alkaline earth metal salts and, particularly, calcium, magnesium, ammonium, sodium, lithium, zinc, potassium, and iron salts. The present invention can also include quaternary ammonium salts of the compounds.

As used herein, the terms "prevention" or "preventing" mean a reduction of the risk of acquiring a particular disease, condition, or disorder.

As used herein, the term "prodrug" means a derivative of a known direct acting drug, which derivative has enhanced delivery characteristics and therapeutic value as compared to the drug, and is transformed into the active drug by an enzymatic or chemical process.

As used herein, the term "sedation" means depressed consciousness in which a patient or subject retains the ability to independently and continuously maintain an open airway and a regular breathing pattern, and to respond appropriately and rationally to physical stimulation and verbal commands.

As used herein, the phrase "significant sedation" is consistent with a patient's self-evaluation on the Stanford Sleepiness Scale, with Subject patients rating their degree of sedation as greater than or equal to Level 3, wherein: Level 1=Feeling active, vital, alert, or wide awake; Level 2=Functioning at high levels, but not at peak; able to concentrate; Level 3=Awake, but relaxed; responsive but not fully alert; Level 4=Somewhat foggy, let down; Level 5=Foggy; losing interest in remaining awake; slowed down; Level 6=Sleepy, woozy, fighting sleep; prefer to lie down; or Level 7=No longer fighting sleep, sleep onset soon; having dream-like thoughts. "Significant sedation" also means that the patient or subject experiences sedation of Level 4 or greater on the Ramsay Sedation Scale, wherein: Level 1=Patient is anxious and agitated or restless, or both; Level 2=Patient is cooperative, oriented, and tranquil; Level 3=Patient responds to commands only; Level 4=Asleep; brisk response to light glabellar tap or loud auditory stimulus; Level 5=asleep; sluggish response to light glabellar tap or loud auditory stimulus; Level 6=asleep; no response to painful stimulus. "Significant sedation" also means that the patient or subject experiences sedation of Level 5 or less on the Modified Observer's Assessment of Alertness/Sedation Scale, wherein: Level 6=Appears alert and awake, responds readily to name spoken in normal tone; Level 5=Appears asleep but responds readily to name spoken in normal tone; Level 4=lethargic response to name spoken in normal tone; Level 3=responds only after name is called loudly or repeatedly; Level 2=responds only after mild prodding or shaking; Level 1=does not respond to mild prodding or shaking; and Level 0=does not respond to noxious stimulus.

As used herein, the phrase "solubilizing agent" means agents that result in formation of a micellar solution or a true solution of the drug.

As used herein, the term "solution/suspension" means a liquid composition wherein a first portion of the active agent is present in solution and a second portion of the active agent is present in particulate form, in suspension in a liquid matrix.

As used herein, the phrase "substantially isolated" means a compound that is at least partially or substantially separated from the environment in which it is formed or detected.

As used herein, the phrase "therapeutically effective amount" generally means the amount of active compound or pharmaceutical agent that elicits the biological or medicinal response that is being sought in a tissue, system, animal, individual or human by a researcher, veterinarian, medical doctor or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be determined based on the age, health, size and sex of the subject. Optimal amounts can also be determined based on monitoring of the subject's response to treatment. In some embodiments, the therapeutically effective amount is a specific amount or range described herein.

As used herein, the terms "treat," "treated," or "treating" mean both therapeutic treatment or prophylactic or preventative measures wherein the object is to prevent or slow down (lessen) an undesired physiological condition, disorder or disease, or obtain beneficial or desired clinical results. For purposes of this invention, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant analgesic response without excessive levels of side effects, such as, but not limited to, significant sedation. Thus, "treatment of pain" or "treating pain" means an activity that prevents, alleviates or ameliorates any of the primary phenomena or secondary symptoms associated with pain.

As used herein "without significant sedation" means that the patient experiences a level of sedation not greater than Level 3 on the Ramsay Sedation Scale, not greater than Level 2 on the Stanford Sleepiness Scale, and/or not less than Level 6 on the Modified Observer's Assessment Of Alertness/Sedation Scale.

It is further appreciated that certain features described herein, which are, for clarity, described in the context of separate embodiments, can also be provided in combination in a single embodiment. Conversely, various features which are, for brevity, described in the context of a single embodiment, can also be provided separately or in any suitable subcombination.

Dexmedetomidine is a specific alpha-2-adrenergic receptor agonist that causes sedation, anesthesia, and analgesia in mammals. In humans, dexmedetomidine is commercially available for sedation of initially intubated and mechanically ventilated patients during treatment in an intensive care setting, as well as sedation of non-intubated patients prior to or during surgical and other procedures. See, e.g., U.S. Pat. Nos. 6,716,867 and 6,313,311, each of which are hereby incorporated by reference in their entirety.

Dexmedetomidine contains a basic nitrogen atom capable of forming a pharmaceutically acceptable salt with a pharmaceutically acceptable acid. Pharmaceutically acceptable salts, in this respect, refers to the relatively non-toxic, inorganic, and organic acid addition salts of dexmedetomidine. These salts may be prepared in situ during final isolation and purification of dexmedetomidine or by separately reacting purified dexmedetomidine in its free base form with a suitable organic or inorganic acid, and thereafter isolating the salt thus formed. Furthermore, the salt may be formed during a manufacturing process to produce the spray formulation. Representative pharmaceutically acceptable salts include, but are not limited to, the hydrohalide (including hydrobromide and hydrochloride), sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, 2-hydroxyethylsulfonate, and laurylsulphonate salts, and the like. See, e.g., "Pharmaceutical Salts," Berge et al., J. Pharm. Sci., 1977, 66, 1-19. Dexmedetomidine hydrochloride is an example of a pharmaceutically acceptable salt. Use of dexmedetomidine hydrochloride may be used, in part because, in some cases, the hydrochloride salt has greater water solubility and stability against oxidation by ambient oxygen.

Dexmedetomidine derivatives include covalent modifications that create a prodrug. Upon administration, the prodrug derivative undergoes chemical modification by the mammal that yields dexmedetomidine. Prodrugs may be used to favorably alter the biodistribution or the pharmacokinetics of dexmedetomidine or to produce other desirable characteristics. For example, a reactive nitrogen of dexmedetomidine may be derivatized with a functional group that is cleaved, enzymatically or non-enzymatically, reductively, oxidatively, or hydrolytically, to reveal the active pharmaceutical ingredient. Uses of certain types of prodrugs are known (see, e.g., R. B. Silverman, 1992, "The Organic Chemistry of Drug Design and Drug Action," Academic Press, Chp. 8). For example, prodrugs may be prepared in situ during the final isolation and purification of the compounds, or by separately reacting the purified compound in its free base form with a suitable derivatizing agent.

The present disclosure describes the surprising and unexpected result(s) that an intranasal formulation of dexmedetomidine, or a pharmaceutically acceptable salt thereof, can be developed for the treatment of pain that has a reduced time to the onset of pain relief corresponding to $C_{plasma}$, a $C_{max}$, and a reduced time to $T_{max}$, that can lead to pain relief or prevention without sedation or significant sedation in a mammal.

The present invention provides methods of treating or preventing pain without significant sedation in a mammal comprising intranasally administering an intranasally effective amount of dexmedetomidine, or a pharmaceutically acceptable salt thereof, to the mammal. The dexmedetomidine, or a pharmaceutically acceptable salt thereof, or compositions comprising the same, can be administered in any conventional manner such that the composition is administered intranasally. That is, the composition is contacted with the nasal cavity. The compositions can also be administered, for example, by implanting the composition so that it is absorbed intranasally.

In some embodiments, the dexmedetomidine, or pharmaceutically acceptable salt thereof, is absorbed through the nasal mucosa. In some embodiments, at least 10%, at least 20%, at least 30%, at least 40%, at least 50%, at least 60%, at least 70%, at least 80%, at least 90%, at least 95%, at least 96%, at least 97%, at least 98%, or at least 99% of the composition is absorbed through the nasal mucosa. In some embodiments, dexmedetomidine, or a pharmaceutically acceptable salt thereof, is not absorbed through the oral mucosa.

In some embodiments, the method comprises treating or preventing pain relief without sedation or significant sedation. In some embodiments, the level of sedation is no greater than Level 1 on the Ramsay Sedation Scale. In some embodiments, the level of sedation is no greater than Level 2 on the Ramsay Sedation Scale. In some embodiments, the level of sedation is no greater than Level 3 on the Ramsay Sedation Scale. In some embodiments, the level of sedation is no greater than Level 1 on the Stanford Sleepiness Scale. In some embodiments, the level of sedation is no greater than Level 2 on the Stanford Sleepiness Scale. In some embodiments, the level of sedation is no less than Level 6 on the Modified Observer's Assessment of Alertness/Sedation Scale. In some embodiments, during the hour immediately after administration of the dexmedetomidine, or pharmaceutically acceptable salt thereof, to the mammal or human, the level of sedation is not greater than Level 3 on the Ramsay Sedation Scale. In some embodiments, during the hour immediately after administration of the dexmedetomidine, or pharmaceutically acceptable salt thereof, to the mammal or human, the level of sedation is not greater than Level 2 on the Ramsay Sedation Scale. In some embodiments, during the hour immediately after administration of the dexmedetomidine, or pharmaceutically acceptable salt thereof, to the mammal or human, the level of sedation is not greater than Level 1 on the Ramsay Sedation Scale. In some embodiments, during the hour immediately after administration of the dexmedetomidine, or pharmaceutically acceptable salt thereof, to the mammal or human, the level of sedation is not greater than Level 2 on the Stanford Sleepiness Scale. In some embodiments, during the hour immediately after administration of the dexmedetomidine, or pharmaceutically acceptable salt thereof, to the mammal or human, the level of sedation is not greater than Level 1 on the Stanford Sleepiness Scale. In some embodiments, during the hour immediately after administration of the dexmedetomidine, or pharmaceutically acceptable salt thereof, to the mammal or human, the level of sedation is not less than Level 6 on the Modified Observer's Assessment Of Alertness/Sedation Scale.

In some embodiments, the pain is idiopathic pain. In some embodiments, the idiopathic pain is neuralgia, myalgia, hyperalgia, hyperpathia, neuritis, or neuropathy. In some embodiments, the pain is associated with or caused by cancer, viral infection, physical trauma, arthritis, headache, migraine, or lower back pain. In some embodiments, the physical trauma is associated with or caused by surgery, a burn, blunt force trauma, or other trauma that can cause pain, such as being in an accident.

In some embodiments, the means and methods of administering the compositions described herein are known. The means and methods for administration are known in the art and an artisan can refer to various pharmacologic references for guidance (see, for example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980)).

In some embodiments, the amount of compound to be administered is that amount which is therapeutically effective or intranasally effective. The dosage to be administered can depend on the characteristics of the subject being treated, e.g., the particular animal treated, age, weight, health, types of concurrent treatment, if any, and frequency of treatments, and can be easily determined by one of skill in the art (e.g., by the clinician). The selection of the specific dose regimen can be selected or adjusted or titrated by the clinician according to methods known to the clinician to obtain the desired clinical response or as they are described herein. Further, the amount of a compound described herein that will be effective in the treatment and/or prevention of a particular disease, condition, or disorder will depend on the nature and extent of the disease, condition, or disorder, and can be determined by standard clinical techniques. In addition, in vitro or in vivo assays may optionally be employed to help identify optimal dosage ranges. The dosages can be, for example, the doses described herein.

The compounds, or composition comprising the same, can be administered in various dosage forms suitable for intranasal administration. The dosage amount present in the dosage form can be a pharmaceutically or intranasally effective amount. In some embodiments, the effective amount is an amount sufficient to treat or prevent pain. In some embodiments, the effective amount is an amount that does not produce sedation. In some embodiments, the effective amount does not produce significant sedation. In some embodiments, the effective amount is an amount sufficient to treat or prevent pain, yet does not produce sedation or significant sedation.

$C_{plasma}$ is the concentration of dexmedetomidine in the plasma of a mammal or human at a particular time after administration. In some embodiments, the intranasally effective amount of dexmedetomidine, or pharmaceutically acceptable salt thereof, produces a $C_{plasma}$ of about 0.1 ng/ml within about 15 minutes to about 20 minutes of administration and has an analgesic effect without significant sedation. Thus, in some embodiments, within about 15 minutes to about 20 minutes of administration of dexmedetomidine, or pharmaceutically acceptable salt thereof, to a mammal or human, the mammal or human will have a $C_{plasma}$ of about 0.1 ng/ml. In some embodiments, the $C_{plasma}$ is from about 0.09 ng/ml to about 0.11 ng/ml, from about 0.08 ng/ml to about 0.12 ng/ml, from about 0.06 ng/ml to about 0.09 ng/ml, from about 0.07 ng/ml to about 0.09 ng/ml, or from about 0.08 ng/ml to about 0.09 ng/ml. In some embodiments, the targeted Co. is reached within about 8 minutes to about 30 minutes, within about 10 minutes to about 30 minutes, within about 12 minutes to about 30 minutes, within about 8 minutes to about 20 minutes, within about 10 minutes to about 20 minutes, within about 12 minutes to about 20 minutes, within about 8 minutes to about 15 minutes, within about 10 minutes to about 15 minutes, within about 12 minutes to about 15 minutes, within about 8 minutes to about 10 minutes, within about 8 minutes to about 12 minutes, within about 15 minutes to about 20 minutes, within about 15 minutes to about 20 minutes, within about 15 minutes, within about 12 minutes, within about 10 minutes, or within about 8 minutes of administration and has an analgesic effect without significant sedation. This time point can reflect the onset of pain relief (i.e., an analgesic effect).

In some embodiments, the onset of pain relief is less than about 60 minutes, less than about 55 minutes, less than about 50 minutes, less than about 45 minutes, less than about 40 minutes, less than about 35 minutes, less than about 30 minutes, less than about 25 minutes, less than about 20 minutes, less than about 15 minutes, less than about 12 minutes, less than about 10 minutes, about 15 minutes, about 12 minutes, about 10 minutes, or about 8 minutes. The onset of pain relief is the time when a mammal feels that the pain is less than prior to the administration of a compound or composition described herein. In some embodiments, the pain relief is complete and the mammal no longer feels the pain that was being relieved.

The present invention also provides methods of treating or preventing pain without significant sedation in an adult human comprising intranasally administering an intranasally effective amount of dexmedetomidine, or a pharmaceutically acceptable salt thereof, to the adult human whereby the intranasally effective amount of dexmedetomidine, or pharmaceutically acceptable salt thereof, does not produce significant sedation in the adult within a period of time of about two hours after administration and has an analgesic effect within the period of time. In some embodiments, significant sedation in the adult is not produced within a period of time of about 1.5 hours after administration, but yet has an analgesic effect within the period of time. In some embodiments, significant sedation in the adult is not produced within a period of time of about 1.0 hours after administration, but yet has an analgesic effect within the period of time. In some embodiments, significant sedation in the adult is not produced within a period of time of about 45 minutes after administration, but yet has an analgesic effect within the period of time. In some embodiments, significant sedation in the adult is not produced within a period of time from about 30 minutes to about of about 1.5 hours after administration, but yet has an analgesic effect within the period of time. In some embodiments, significant sedation in the adult is not produced within a period of time from about 40 minutes to about 75 minutes after administration, but yet has an analgesic effect within the period of time. In some embodiments, significant sedation in the adult is not produced within a period of time from about 45 minutes to about 70 minutes after administration, but yet has an analgesic effect within the period of time. In some embodiments, significant sedation in the adult is not produced within a period of time from about 50 minutes to about 65 minutes after administration, but yet has an analgesic effect within the period of time. In some embodiments, significant sedation in the adult is not produced within a period of time from about 55 minutes to about 60 minutes after administration, but yet has an analgesic effect within the period of time.

The present invention also provides methods of treating or preventing pain without significant sedation in a mammal comprising intranasally administering dexmedetomidine, or a pharmaceutically acceptable salt thereof, to a single nostril of the mammal, particularly a human. Administration to a single nostril means that the entire unit dose is administered to a single nostril as compared to a portion of the unit dose being administered to both nostrils. In some embodiments, the unit dose is only administered to a single nostril. That is, if a dosage is given every 4 hours, the dosage is administered to only a single nostril every 4 hours. The single nostril to which the compositions are administered may alternate between the two nostrils, however. In some embodiments, the methods comprise not administering dexmedetomidine or a pharmaceutically acceptable salt thereof or a composition described herein to more than one nostril (e.g., two nostrils).

The present invention also provides methods of treating or preventing pain without significant sedation in a mammal comprising intranasally spraying in the mammal a pharmaceutical composition comprising dexmedetomidine, or a pharmaceutically acceptable salt thereof, wherein the spray comprises droplets which have a Dv90 of less than about 150 µm. In some embodiments, the spray comprises droplets which have a Dv90 of less than about 125 µm. In some embodiments, the spray comprises droplets which have a Dv90 of less than about 100 µm. In some embodiments, the spray comprises droplets which have a Dv90 from about 60 µm to about 150 µm, from about 60 µm to about 125 µm, or from about 60 µm to about 100 µm. In some embodiments, the spray comprises droplets which have a Dv90 of more than about 40 µm. In some embodiments, the spray comprises droplets which have a Dv90 of more than about 50 µm. In some embodiments, the spray comprises droplets which have a Dv90 of more than about 60 µm. In some embodiments, the spray comprises droplets which have a Dv90 of more than about 70 µm.

In some embodiments, the present invention provides methods of treating or preventing pain without significant sedation in a mammal comprising intranasally administering an intranasally effective amount of dexmedetomidine, or a pharmaceutically acceptable salt thereof, to the mammal whereby the intranasally effective amount of dexmedetomidine, or pharmaceutically acceptable salt thereof, produces a $C_{plasma}$ of about 0.1 ng/ml within about 15 minutes to about 20 minutes of administration and has an analgesic effect without significant sedation, and whereby the intranasally effective amount of dexmedetomidine, or pharmaceutically acceptable salt thereof, does not produce significant sedation within a period of time of about two hours after administration and has an analgesic effect within the period of time.

In some embodiments, the present invention provides methods of treating or preventing pain without significant sedation in a mammal comprising intranasally administering an intranasally effective amount of dexmedetomidine, or a pharmaceutically acceptable salt thereof, to a single nostril of the mammal, particularly a human, whereby the intranasally effective amount of dexmedetomidine, or pharmaceutically acceptable salt thereof, produces a $C_{plasma}$ of about 0.1 ng/ml within about 15 minutes to about 20 minutes of administration and has an analgesic effect without significant sedation.

In some embodiments, the present invention provides methods of treating or preventing pain without significant sedation in a mammal comprising intranasally spraying an intranasally effective amount of dexmedetomidine, or a pharmaceutically acceptable salt thereof, to the mammal whereby the intranasally effective amount of dexmedetomidine, or pharmaceutically acceptable salt thereof, produces a $C_{plasma}$ of about 0.1 ng/ml within about 15 minutes to about 20 minutes of administration and has an analgesic effect without significant sedation, and wherein the spray comprises droplets which have a Dv90 of less than about 150 µm.

In some embodiments, the present invention also provides methods of treating or preventing pain without significant sedation in an adult human comprising intranasally administering an intranasally effective amount of dexmedetomidine, or a pharmaceutically acceptable salt thereof, to a single nostril of the adult human, whereby the intranasally effective amount of dexmedetomidine, or pharmaceutically acceptable salt thereof, does not produce significant sedation in the adult within a period of time of about two hours after administration and has an analgesic effect within the period of time.

In some embodiments, the present invention also provides methods of treating or preventing pain without significant sedation in an adult human comprising intranasally spraying an intranasally effective amount of dexmedetomidine, or a pharmaceutically acceptable salt thereof, to the adult human whereby the intranasally effective amount of dexmedetomidine, or pharmaceutically acceptable salt thereof, does not produce significant sedation in the adult within a period of time of about two hours after administration and has an analgesic effect within the period of time, and wherein the spray comprises droplets which have a Dv90 of less than about 150 µm.

In some embodiments, the present invention also provides methods of treating or preventing pain without significant sedation in a mammal comprising intranasally spraying dexmedetomidine, or a pharmaceutically acceptable salt thereof, to a single nostril of the mammal, particularly a human, wherein the spray comprises droplets which have a Dv90 of less than about 150 µm.

In some embodiments, the present invention provides methods of treating or preventing pain without significant sedation in a human comprising intranasally administering an intranasally effective amount of dexmedetomidine, or a pharmaceutically acceptable salt thereof, to a single nostril of the human whereby the intranasally effective amount of dexmedetomidine, or pharmaceutically acceptable salt thereof, produces a $C_{plasma}$ of about 0.1 ng/ml within about 15 minutes to about 20 minutes of administration and has an analgesic effect without significant sedation, whereby the intranasally effective amount of dexmedetomidine, or pharmaceutically acceptable salt thereof, does not produce significant sedation in the human within a period of time of about two hours after administration and has an analgesic effect within the period of time.

In some embodiments, the present invention provides methods of treating or preventing pain without significant sedation in a mammal comprising intranasally spraying an intranasally effective amount of dexmedetomidine, or a pharmaceutically acceptable salt thereof, to the mammal whereby the intranasally effective amount of dexmedetomidine, or pharmaceutically acceptable salt thereof, produces a $C_{plasma}$ of about 0.1 ng/ml within about 15 minutes to about 20 minutes of administration and has an analgesic effect without significant sedation, whereby the intranasally effective amount of dexmedetomidine, or pharmaceutically acceptable salt thereof, does not produce significant sedation in the mammal within a period of time of about two hours after administration and has an analgesic effect within the period of time, and wherein the spray comprises droplets which have a Dv90 of less than about 150 µm.

In some embodiments, the present invention provides methods of treating or preventing pain without significant sedation in a human comprising intranasally spraying an intranasally effective amount of dexmedetomidine, or a pharmaceutically acceptable salt thereof, to a single nostril of the human whereby the intranasally effective amount of dexmedetomidine, or pharmaceutically acceptable salt thereof, produces a $C_{plasma}$ of about 0.1 ng/ml within about 15 minutes to about 20 minutes of administration and has an analgesic effect without significant sedation, wherein the spray comprises droplets which have a Dv90 of less than about 150 µm.

In some embodiments, the present invention also provides methods of treating or preventing pain without significant sedation in a human comprising intranasally spraying an intranasally effective amount of dexmedetomidine, or a pharmaceutically acceptable salt thereof, to a single nostril of the human whereby the intranasally effective amount of dexmedetomidine, or pharmaceutically acceptable salt thereof, does not produce significant sedation in the human within a period of time of about two hours after administration and has an analgesic effect within the period of time, wherein the spray comprises droplets which have a Dv90 of less than about 150 µm.

In some embodiments, the present invention provides methods of treating or preventing pain without significant sedation in a human comprising intranasally spraying an intranasally effective amount of dexmedetomidine, or a pharmaceutically acceptable salt thereof, to a single nostril of the human whereby the intranasally effective amount of dexmedetomidine, or pharmaceutically acceptable salt thereof, produces a $C_{plasma}$ of about 0.1 ng/ml within about 15 minutes to about 20 minutes of administration and has an analgesic effect without significant sedation, whereby the intranasally effective amount of dexmedetomidine, or pharmaceutically acceptable salt thereof, does not produce significant sedation in the human within a period of time of about two hours after administration and has an analgesic effect within the period of time, and wherein the spray comprises droplets which have a Dv90 of less than about 150 µm.

In any of the methods described herein, the plasma $C_{max}$ of dexmedetomidine is from about 0.08 ng/ml to about 0.25 ng/ml, about 0.08 ng/ml to about 0.2 ng/ml, from about 0.1 ng/ml to about 0.2 ng/ml, from about 0.08 ng/ml to about 0.15 ng/ml, from about 0.1 ng/ml to about 0.15 ng/ml, or from about 0.15 ng/ml to about 0.2 ng/ml. In some embodiments, the plasma $C_{max}$ of dexmedetomidine is from about 0.08 ng/ml to about 0.2 ng/ml. In some embodiments, the plasma $C_{max}$ of dexmedetomidine is about 0.15 ng/ml. In some embodiments, the plasma $C_{max}$ of dexmedetomidine is about 0.2 ng/ml. In some embodiments, the plasma $C_{max}$ of dexmedetomidine is about 0.25 ng/ml.

In any of the methods described herein, the $T_{max}$ is less than about 60 minutes, less than about 50 minutes, less than about 40 minutes, less than about 35 minutes, or less than about 30 minutes. In some embodiments, the $T_{max}$ is from about 20 minutes to about 60 minutes, from about 20 minutes to about 50 minutes, from about 20 minutes to about 40 minutes, from about 20 minutes to about 30 minutes, from about 30 minutes to about 60 minutes, from about 30 minutes to about 50 minutes, from about 30 minutes to about 40 minutes, from about 40 minutes to about 60 minutes, from about 40 minutes to about 50 minutes, or from about 50 minutes to about 60 minutes. In some embodiments, the $T_{max}$ of dexmedetomidine is less than about 1 hour. In some embodiments, the $T_{max}$ is less than about 50 minutes.

In any of the methods described herein, the compound or composition can be administered according to a specific schedule. In some embodiments, the composition is administered about every 2 hours, about every 4 hours, about every 6 hours, about every 8 hours, about every 10 hours, about every 12 hours, or about every 24 hours. The composition can also be administered as needed. In some embodiments, dexmedetomidine, or pharmaceutically acceptable salt thereof, or composition comprising the same, is administered about every 6 hours.

In any of the methods described herein, the dexmedetomidine, or pharmaceutically acceptable salt thereof, is administered as a unit dose of about 10 µg to about 100 µg, from about 10 µg to about 90 µg, from about 10 µg to about 80 µg, from about 10 µg to about 70 µg, from about 10 µg to about 60 µg, from about 10 µg to about 50 µg, from about 10 µg to about 40 µg, from about 10 µg to about 30 µg, from about 10 µg to about 20 µg, from about 25 µg to about 100, from about 25 µg to about 90 µg, from about 25 µg to about 80 µg, from about 25 µg to about 70 µg, from about 25 µg to about 60 µg, from about 25 µg to about 50 µg, from about 25 µg to about 40 µg, from about 25 µg to about 35 µg, from about 25 µg to about 30 µg, from about 30 µg to about 45 µg, from about 35 µg to about 45 µg, from about 30 µg to about 40 µg, or from about 25 µg to about 45 µg. In some embodiments, the dexmedetomidine, or pharmaceutically acceptable salt thereof, is administered as a unit dose of about 10 µg, about 15 µg, about 20 µg, about 25 µg, about 30 µg, about 35 µg, about 40 µg, about 45 µg, about 50 µg, about 55 µg, about 60 µg, about 70 µg, about 75 µg, about 80 µg, about 85 µg, about 90 µg, about 95 µg, or about 100 µg. In some embodiments, the dexmedetomidine, or pharmaceutically acceptable salt thereof, is administered as a unit dose of less than about 100 µg, less than about 90 µg, less than about 80 µg, less than about 70 µg, less than about 60 µg, less than about 50 µg, less than about 40 µg, less than about 30 µg, less than about 20 µg, or less than about 10 µg. In some embodiments, the dexmedetomidine, or pharmaceutically acceptable salt thereof, is administered as a unit dose of about 10 µg, about 25 µg, about 30 µg, about 35 µg, about 40 µg, about 50 µg, about 75 µg, or about 100 µg. As discussed herein, the unit dose can be administered in many different manners. In some embodiments the unit dose is administered by a single nasal spray. In some embodiments the unit dose is administered by a single nasal spray using a single dose spray device requiring no priming. The single dose can be administered through a single actuation of a nasal spray device. An examples of spray device that does not require priming includes, but is not limited to, Aptar Unitdose Intranasal Systems. The spray device can, in some embodiments, deliver a volume of about 100 µl. In some embodiments, the volume is about 10, 20, 30, 40, 50, 60, 70, 80, or 90 µl. In some embodiments, the volume is from about 10-100, about 20-100, about 30-100, about 40-100, about 50-100, about 60-100, about 70-100, about 80-100, about 90-100 µl.

In any of the methods described herein, the method comprises having no effect or having minimal effect on blood pressure after administration. In some embodiments, there is no effect on blood pressure within the hour immediately after a compound described herein is administered. In some embodiments, there is only minimal effect on blood pressure within the hour immediately after a compound described herein is administered. In some embodiments, the resting mean arterial blood pressure of the mammal is not effected by more than about 5 mmHg, more than about 10 mmHg, more than about 15 mmHg, more than about 20 mmHg, more than about 25 mmHg, or more than about 30 mmHg. The mean arterial blood pressure can be measured by any method known to one of skill in the art. In some embodiments, there is no or minimal effect on blood pressure after administration of the dexmedetomidine, or pharmaceutically acceptable salt thereof.

In any of the methods described herein, the method further comprises administering in simultaneous, alternating, or sequential combination to the human or mammal one or more additional therapeutic agents. The one or more additional therapeutic agents is chosen from an analgesic, such as an opioid analgesic (e.g. morphine, oxycodone, hydromorphone, etc.), a synthetic opioid-like analgesic (e.g. meperidine, fentanyl, pentazocine, butorphanol, etc.), or a non-opioid analgesic (e.g. NSAIDs, ketamine, salicylates, steroids, etc.); a vitamin; a vasodilator; a benzodiazepine (e.g. clonazepam, alprazolam, lorazepam, etc.); a triptan (and other compounds for migraine headaches); an anti-convulsant (e.g. pregabalin, valproic acid, gabapentin, etc.); an anti-depressant (e.g. tricyclics such as amitriptyline, nortriptyline, etc.; serotonin and norepinephrine reuptake inhibitors such as duloxetine, fluoxetine, venlafaxine, etc.); an anti-nausea medication (e.g. metoclopramide, prochlorperazine, ondansetron, granisetron, etc.); and an anti-hypertensive (e.g. beta blockers such as propranolol and calcium channel blockers such as verapamil, etc.).

The present invention also provides any one or more of the compositions described herein for treating pain in a mammal without significant sedation.

The present invention also provides any one or more of the compositions described herein for use in the manufacture of a medicament for treating pain in a mammal without significant sedation.

In any of the methods described herein, the dexmedetomidine, or pharmaceutically acceptable salt thereof, can be administered intranasally with a device. In some embodiments, the device is a metered dose device. In some embodiments, the metered dose device is a multi-dose, unit dose, or bi-dose device.

In some embodiments, the device is suitable for intranasal administration. Any device that is suitable for intranasal administration can be used. In some embodiments, the device is a metered dose device. The metered dose device can deliver a specific dosage amount of the composition. The metered dose device can be a unit-dose, bi-dose, or a multi-dose device. The pharmaceutically effective amount that can be administered using a metered dose device can be a unit dose device. The metered dose can, in some embodiments, be a device that can deliver a pharmaceutical composition intranasally. Examples of metered dose devices include, but are not limited to, devices that are pump devices, mechanical devices, pressurized devices, and/or electromechanical devices. Examples of a metered dose device include, but are not limited to, a spray pump, a pre-compression nasal spray pump, a metered valve device, an actuated spray device, a side actuated spray device, a syringe nasal spray device (e.g. a syringe that has an atomizer to deliver a spray to the nasal cavity), a mucosal atomization device, an electromechanical pump device (with and without a counter), and the like. Examples of metered dose devices also include, but are not limited to, devices manufactured by Aptar Pharma (Congers, N.Y.) and are commercially available. Examples of metered dose devices also include, but are not limited to, UDS (Aptar Pharma), BDS (Aptar Pharma), eDevices (Aptar Pharma), Equadel (Aptar Pharma), Latitude (Aptar Pharma), DF30 (Aptar Pharma), VP7 (Aptar Pharma), Classic Nasal Device (Aptar Pharma), MAD Nasal Drug Device (Wolf Tory Medical, Inc.), BD Accuspray SCF™ (Becton Dickinson), and the like. Another example includes, but is not limited to, an Aptar Unitdose Intranasal System.

Analgesic, intranasal formulations of dexmedetomidine, or a pharmaceutically acceptable salt or derivative thereof, can be administered in metered dosages so that a predetermined amount of the active pharmaceutical ingredient is properly administered to the subject in a pharmaceutically effective amount. For example, the intranasal formulation may be packaged as a bulk liquid containing multiple doses in a pump spray system comprising a sealed container fitted with a metering pump. In some embodiments, a subject is treated by intranasal self-administration, such as by one or more actuations from a spray pump. An advantage of intranasal delivery examples herein is the ability to titrate subjects by single doses as supplied by single, discrete actuations. This advantage is typically absent from other forms of drug delivery (e.g., patches, lozenges, tablets, and suppositories) in which a one-size-fits-all dosage is administered in a standard regimen. Additional advantages of intranasal formulations include its ease of use, especially when self-administered absent an attending health care professional.

In some embodiments, the metered dose device is a spray delivery device, which includes a base unit, a discharge actuator, an orifice for the formulation to be release from the device, and a reservoir. The reservoir can be filled with dexmedetomidine, or pharmaceutically acceptable salt thereof, and optionally other excipients, such as those described throughout the present application, prior to dispensing to the patient, e.g., at the manufacturing site. The reservoir can contain a measured amount of dexmedetomidine, or pharmaceutically acceptable salt thereof, or derivative thereof, to be discharged upon activation. The reservoir body may be any acceptable material, for example, formed simply by a section of a cylindrical hollow of a plastic, steel, such as stainless steel, transparent material, or the like so that its production is very simple. An actuator, which is movable relative to the orifice for activating discharge, may be provided on or with the device. In the course of the actuating movement, the reservoir opens, e.g. by puncturing, to administer a single dosage through an orifice. During a part of the actuating travel following the starting position an elevated pressure is built up. In a subsequent portion of the actuating movement continuing in the same direction, the medium may be relieved of the pressure at one of the sides and communicated to an orifice. In such a manner, the medium is pushed from the reservoir and through the orifice by the action of pressure.

In some embodiments, as the liquid formulation leaves the orifice, the liquid droplets follow a trajectory which is influenced by the orifice shape, as well as by pressure asserted. In some embodiments, the droplet size, spray geometry, and the spray pattern are dependent on the design of the pump and/or the properties of the formulation. In some embodiments, the orientation of the actuator, pump design, and the properties of the formulation will influence the spray symmetry and the shape. The spray pattern may also be optimized to disperse the droplets over a wider pathway thereby increasing the surface area through which the compound can be absorbed. The device may further be designed to facilitate ease of patient use and placement of the administered spray to specific regions of the nasal mucosa.

Pump action sprays can be characterized by the application of external pressure for actuation, for example, external manual, mechanical or electrically initiated pressure. This is in contrast to pressurized systems, e.g., propellant-driven aerosol or compressed gas sprays, where actuation is typically achieved by controlled release of pressure, such as by controlled opening of a valve. In some embodiments, pump sprays are used. Use of a pump spray with the formulations herein allows for the administration of droplets or particles having a small mean diameter and a controllable size distribution of droplets. In some embodiments, pressurized systems containing a reservoir of pressurized propellant gas (e.g., carbon dioxide, nitrogen, chlorofluorocarbons, hydrofluoroalkanes, etc.) may produce suitable particles or droplets. Liquid droplets or particles having a diameter that is too small have the potential to enter into the lungs of a subject upon administration. In some embodiments, the droplet size of the delivered formulations further provides for an increase in surface area by being sprayed intranasally as opposed to being placed in a nostril, for example, with a dropper. The size of the spray particles and shape of the spray pattern also may contribute to whether the active ingredient is absorbed into body systems in addition to the nasal mucosa (e.g., lungs).

As described herein, the spray pump device may be pre-metered or, alternately, the device may be device-metered. Pre-metered dose devices may contain previously measured doses or a dose fraction in some type of units (e.g., single unit dose amount of solution, single or multiple blisters or other cavities) that may be included in the device during manufacture or by the patient before use. Typical device-metered units have a reservoir containing a formulation sufficient for multiple doses that are delivered as metered sprays by the device itself when activated by the patient. The device may be metered both in the amount of drug substance delivered (i.e., the dosage per actuation), as well as the length of time between each dosage. Limiting the time between each dosage can prevent over-use by limiting how often a dosage can be delivered to the patient.

The embodiments of the devices described herein, is not intended as limiting. In some embodiments, the formulations containing dexmedetomidine may alternately or additionally be provided as other intranasal dosage forms. For example, the intranasal composition may be provided as a liquid compatible with administration by a dropper or similar device. The intranasal formulation can also be provided as a powder to be administered into the nasal cavity. The formulations can be, for example, packaged in pharmaceutically acceptable unit dose ampules with snap-off tops to permit the opened ampule to be inserted into the patient's nasal cavity to dispense a single dose of the formulation.

In yet another embodiment, the compounds can be delivered in a controlled release system. In one embodiment, a pump may be used (see Langer, supra; Sefton, CRC Crit. Ref Biomed. Eng., 1987, 14, 201; Buchwald et al., Surgery, 1980, 88, 507 Saudek et al., N. Engl. J. Med., 1989, 321, 574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger et al., J. Macromol. Sci. Rev. Macromol. Chem., 1983, 23, 61; see, also Levy et al., Science, 1985, 228, 190; During et al., Ann. Neurol., 1989, 25, 351; Howard et al., J. Neurosurg., 1989, 71, 105). Other controlled-release systems discussed in the review by Langer, Science, 1990, 249, 1527-1533 may be used and can be adapted for intranasal administration.

In some embodiments, the aqueous dexmedetomidine intranasal compositions may be administered as drops or as a fine mist. Administration as a fine mist can improve the reproducibility of dosing by facilitating even deposition of the composition on the nasal mucosa. In some embodiments, a pump device is used to generate a fine mist from the bulk nasal solution composition. Unit-dose and bi-dose devices may be used for dexmedetomidine nasal spray compositions since these devices can limit the total dose and/or number of doses that can be delivered from a single device thus reducing the potential for over-dosing/abuse. Furthermore, the unit-dose and/or bi-dose devices may require less packaged volume to deliver the spray volume by reducing the required amount of solution lost to pump priming. In some embodiments, multi-dose devices are used due to their lower cost of manufacturing and less packaging waste.

The present invention also provides metered dose devices comprising a pharmaceutical composition comprising dexmedetomidine, or a pharmaceutically acceptable salt thereof, wherein the metered dose device delivers a metered dose spray of the pharmaceutical composition intranasally that is analgesic in a mammal without significant sedation.

In some embodiments, the metered dose spray produced by the device comprises droplets comprising dexmedetomidine, or a pharmaceutically acceptable salt thereof, that have a Dv90 of less than about 150 μm. In some embodiments, the spray comprises droplets which have a Dv90 of less than about 125 μm. In some embodiments, the spray comprises droplets which have a Dv90 of less than about 100 μm. In some embodiments, the spray comprises droplets which have a Dv90 from about 60 μm to about 150 μm, from about 60 μm to about 125 μm, or from about 60 μm to about 100 μm.

In some embodiments, the metered dose spray produced by the device comprises a metered dose of dexmedetomidine, or a pharmaceutically acceptable salt thereof, from about 10 μg to about 100 μg, from about 10 μg to about 90 μg, from about 10 μg to about 80 μg, from about 10 μg to about 70 μg, from about 10 μg to about 60 μg, from about 10 μg to about 50 μg, from about 10 μg to about 40 μg, from about 10 μg to about 30 μg, from about 10 μg to about 20 μg, from about 25 μg to about 100, from about 25 μg to about 90 μg, from about 25 μg to about 80 μg, from about 25 μg to about 70 μg, from about 25 μg to about 60 μg, from about 25 μg to about 50 μg, from about 25 μg to about 40 μg, from about 25 μg to about 35 μg, from about 25 μg to about 30 μg, or from about 25 μg to about 45 μg. In some embodiments, the metered dose spray produced by the device comprises a metered dose of 10 μg, about 15 μg, about 20 μg, about 25 μg, about 30 μg, about 35 μg, about 40 μg, about 50 μg, about 55 μg, about 60 μg, about 70 μg, about 75 μg, about 80 μg, about 85 μg, about 90 μg, about 95 μg, or about 100 μg. In some embodiments, the metered dose spray produced by the device comprises a metered dose of less than about 100 μg, less than about 90 μg, less than about 80 μg, less than about 70 μg, less than about 60 μg, less than about 50 μg, less than about 40 μg, less than about 30 μg, less than about 20 μg, or less than about 10 μg. In some embodiments, the metered dose spray produced by the device comprises a metered dose of about 10 μg, about 25 μg, about 35 μg, about 50 μg, about 75 μg, or about 100 μg.

In some embodiments, the metered dose spray produced by the device comprises a volume of less than about 150 μl, less than about 140 μl, less than about 130 μl, less than about 120 μl, less than about 110 μl, less than about 100 μl, less than about 75 μl, or less than about 50 μl. In some embodiments, the metered dose spray produced by the device comprises a volume of about 150 μl, about 140 μl, about 130 μl, about 120 μl, about 110 μl, about 100 μl, about 75 μl, or about 50 μl.

In some embodiments, the metered dose spray produced by the device produces a $C_{plasma}$ in the mammal of from about 0.09 ng/ml to about 0.11 ng/ml, from about 0.08 ng/ml to about 0.12 ng/ml, or about 0.1 ng/ml within about 12 minutes to about 30 minutes, from about 12 minutes to about 20 minutes, from about 15 minutes to about 20 minutes, or within about 15 minutes of administration and has an analgesic effect without significant sedation. In some embodiments, the metered dose spray produced by the device produces a $C_{plasma}$ in the mammal of about 0.1 ng/ml within about 15 minutes to about 20 minutes of administration.

In some embodiments, the metered dose spray produces an onset of pain relief less than about 60 minutes, less than about 55 minutes, less than about 50 minutes, less than about 45 minutes, less than about 40 minutes, less than about 35 minutes, less than about 30 minutes, less than about 25 minutes, less than about 20 minutes, or about 15 minutes.

In some embodiments, the metered dose spray produced by the device does not produce significant sedation in an adult within a period of time of about two hours after administration and has an analgesic effect within the period of time. In some embodiments, significant sedation in the adult is not produced within a period of time of about 1.5 hours after administration, but yet has an analgesic effect within the period of time. In some embodiments, significant sedation in the adult is not produced within a period of time of about 1.0 hours after administration, but yet has an analgesic effect within the period of time. In some embodiments, significant sedation in the adult is not produced within a period of time of about 45 minutes after administration, but yet has an analgesic effect within the period of time. In some embodiments, significant sedation in the adult is not produced within a period of time from about 30 minutes to about of about 1.5 hours after administration, but yet has an analgesic effect within the period of time. In some embodiments, significant sedation in the adult is not produced within a period of time from about 40 minutes to about 75 minutes after administration, but yet has an analgesic effect within the period of time. In some embodiments, significant sedation in the adult is not produced within a period of time from about 45 minutes to about 70 minutes after administration, but yet has an analgesic effect within the period of time. In some embodiments, significant sedation in the adult is not produced within a period of time from about 50 minutes to about 65 minutes after administration, but yet has an analgesic effect within the period of time. In some embodiments, significant sedation in the adult is not produced within a period of time from about 55 minutes to about 60 minutes after administration, but yet has an analgesic effect within the period of time.

In some embodiments, the metered dose spray produced by the device produces a plasma $C_{max}$ in the mammal from about 0.08 ng/ml to about 0.25 ng/ml, from about 0.08 ng/ml to about 0.2 ng/ml, from about 0.1 ng/ml to about 0.25 ng/ml, from about 0.1 ng/ml to about 0.2 ng/ml, from about 0.08 ng/ml to about 0.15 ng/ml, from about 0.1 ng/ml to about 0.15 ng/ml, from about 0.15 ng/ml to about 0.2 ng/ml, or from about 0.15 ng/ml to about 0.25 ng/ml. In some embodiments, the metered dose spray produced by the device produces a plasma $C_{max}$ in the mammal of about 0.08 ng/ml to about 0.25 ng/ml. In some embodiments, the metered dose spray produced by the device produces a plasma $C_{max}$ in the mammal of about 0.08 ng/ml to about 0.2 ng/ml. In some embodiments, the metered dose spray produced by the device produces a plasma $C_{max}$ in the mammal of about 0.15 ng/ml. In some embodiments, the metered dose spray produced by the device produces a plasma $C_{max}$ in the mammal of about 0.08 ng/ml, about 0.1 ng/ml, about 0.2 ng/ml, or about 0.25 ng/ml.

In some embodiments, the metered dose spray produced by the device produces a $T_{max}$ in the mammal of less than about 60 minutes, less than about 50 minutes, less than about 40 minutes, less than about 35 minutes, or less than about 30 minutes. In some embodiments, the metered dose spray produced by the device produces a $T_{max}$ in the mammal from about 20 minutes to about 60 minutes, from about 20 minutes to about 50 minutes, from about 20 minutes to about 40 minutes, from about 20 minutes to about 30 minutes, from about 30 minutes to about 60 minutes, from about 30 minutes to about 50 minutes, from about 30 minutes to about 40 minutes, from about 40 minutes to about 60 minutes, from about 40 minutes to about 50 minutes, or from about 50 minutes to about 60 minutes. In some embodiments, the metered dose spray produced by the device produces a $T_{max}$ in the mammal of less than about 1 hour. In some embodiments, the metered dose spray produced by the device produces a $T_{max}$ in the mammal of less than about 50 minutes.

In some embodiments, the metered dose spray produced by the device during the hour immediately after administration to the mammal produces a level of sedation not greater than Level 1, Level 2, or Level 3 on the Ramsay Sedation Scale. In some embodiments, the metered dose spray produced by the device during the hour immediately after administration to the mammal produces a level of sedation not greater than Level 3 on the Ramsay Sedation Scale. In some embodiments, the metered dose spray produced by the device during the hour immediately after administration to the mammal produces a level of sedation not greater than Level 2 on the Ramsay Sedation Scale.

In some embodiments, the metered dose spray produced by the device during the hour immediately after administration to the mammal produces a level of sedation not greater than Level 1 or Level 2 on the Stanford Sleepiness Scale. In some embodiments, the metered dose spray produced by the device during the hour immediately after administration to the mammal produces a level of sedation not greater than Level 2 on the Stanford Sleepiness Scale.

In some embodiments, the metered dose spray produced by the device during the hour immediately after administration to the mammal produces a level of sedation not less than Level 6 on the Modified Observer's Assessment Of Alertness/Sedation Scale.

In some embodiments, the metered dose spray produced by the device has no or minimal effect on the blood pressure of the mammal after administration. In some embodiments, the metered dose spray produced by the device has no effect on blood pressure within the hour immediately after a compound described herein is administered. In some embodiments, the metered dose spray produced by the device has only minimal effect on blood pressure within the hour immediately after a compound described herein is administered. In some embodiments, the resting mean arterial blood pressure of the mammal is not effected by more than about 5 mmHg, more than about 10 mmHg, more than about 15 mmHg, more than about 20 mmHg, more than about 25 mmHg, or more than about 30 mmHg.

In some embodiments, any of the compositions described herein can further comprise one or more other therapeutic agents. The one or more additional therapeutic agents is chosen from an analgesic, such as an opioid analgesic (e.g. morphine, oxycodone, hydromorphone, etc.), a synthetic opioid-like analgesic (e.g. meperidine, fentanyl, pentazocine, butorphanol, etc.), or a non-opioid analgesic (e.g. NSAIDs, ketamine, salicylates, steroids, etc.); a vitamin; a vasodilator; a benzodiazepine (e.g. clonazepam, alprazolam, lorazepam, etc.); a triptan (and other compounds for migraine headaches); an anti-convulsant (e.g. pregabalin, valproic acid, gabapentin, etc.); an anti-depressant (e.g. tricyclics such as amitriptyline, nortriptyline, etc.; serotonin and norepinephrine reuptake inhibitors such as duloxetine, fluoxetine, venlafaxine, etc.); an anti-nausea medication (e.g. metoclopramide, prochlorperazine, ondansetron, granisetron, etc.); and an anti-hypertensive (e.g. beta blockers such as propranolol and calcium channel blockers such as verapamil, etc.).

Examples of other analgesic agents include, but are not limited to, narcotics, NSAIDs, Cox-2 inhibitors, steroids, and the like. Other examples include, but are not limited to, aspirin, codeine, oxycodone, ibuprofen, butalbital, acetaminophen (APAP), caffeine, aspirin, hydrocodone, acetaminophen, propoxyphene n-apap, propoxyphene HCl, butorphanol tartrate, pentazocine-apap, pentazocine-naloxone, tramadol, tramadol extended release, fentanyl, morphine, meperidine HCl, hydromorphone HCl, methadone, levorphanol tartrate, oxymorphone, buprenorphine, celecoxib, rofecoxib, naltrexone, naproxen, flurbiprofen, diclofenac, sulindac, oxaprozin, piroxicam, indomethacin, etodolac, meclofenamate, meloxicam, fenoprofen, ketoprofen, nabumetone, tolmetin, ketorolac tromethamine, salsalate, diflunisal, choline and magnesium salicylates, or any combination thereof. The compounds or salts thereof, and compositions comprising the same, described herein can be administered either alone or in combination (concurrently or serially) with the other pharmaceutical agents. In some embodiments, the compositions described herein can be administered with one or more other analgesic agents.

In some embodiments, the composition further comprises a carrier vehicle. In some embodiments, the pharmaceutical composition further comprises sodium phosphate and/or sodium citrate. In some embodiments, the pharmaceutical composition further comprises sodium citrate, citric acid, and sodium chloride. In some embodiments, the pharmaceutical composition further comprises about 0.2% to about 0.3% (w/w) sodium citrate and about 0.005% to about 0.015% (w/w) citric acid.

In some embodiments, the composition comprises a salt, such as a pharmaceutically acceptable salt. In some embodiments, the composition comprises sodium chloride, potassium chloride, or any combination thereof. In some embodiments, the composition comprises citric acid. In some embodiments, the composition comprises sodium citrate, citric acid, and a salt, including, but not limited to, sodium chloride. In some embodiments, the composition comprises about 0.1% to about 0.5%, from about 0.1% to about 0.4%, from about 0.2% to about 0.5%, from about 0.2% to about 0.4%, from about 0.2% to about 0.3% (w/w) of sodium citrate. In some embodiments, the composition comprises from about 0.005% to about 0.015%, from about 0.005% to about 0.05%, from about 0.005% to about 0.004%, from about 0.005% to about 0.03%, from about 0.005% to about 0.02%, or from about 0.005% to about 0.0175% (w/w) of citric acid.

In some embodiments, the pharmaceutical composition further comprises a chelator or stabilizer that can be used to enhance chemical stability where required. Suitable stabilizers include, but are not limited to, chelating agents or complexing agents, such as, for example, the calcium complexing agent ethylene diamine tetraacetic acid (EDTA), a salt of EDTA, citric acid, chitosan, sorbitol, and tartaric acid. For example, an appropriate amount of EDTA or a salt thereof, e.g., the disodium salt, can be included in the composition to complex excess calcium ions and prevent gel formation during storage. EDTA or a salt thereof can suitably be included in an amount of about 0.01% to about 0.5%. In those embodiments containing a preservative other than EDTA, the EDTA or a salt thereof, more particularly disodium EDTA, can be present in an amount of about 0.025% to about 0.1% by weight. Without being bound by any theory, the chelating agents can prevent multivalent cationic degradation of dexmedetomidine or other components in the composition.

In some embodiments, the intranasal compositions described herein may optionally include a buffering system comprised of an acid/base pair that resists changes in pH. The pH of the compositions can be controlled to limit irritation of the nasal spray. In some embodiments, a solution pH of about 6.0 to about 6.5 can be used to be compatible with the pH of nasal secretions while maintaining the drug in solution. Pharmaceutically acceptable buffers that provide a pH compatible with the nasal mucosa include citrate, phosphate, and the like. In some embodiments, the pH of the composition is less than 7, less than 6.9, less than 6.8, less than 6.7. less than 6.6, less than 6.5, less than 6.4, less than 6.2, or less than 6.1. In some embodiments, the pH of the composition is from about 6 to about 6.1, from about 6 to about 6.2, from about 6 to about 6.3, from about 6 to about 6.4, from about 6 to about 6.5, from about 6 to about 6.6, from about 6 to about 6.7, from about 6 to about 6.8, from about 6 to about 6.9, or from about 6 to about 7.0. In some embodiments, the pH of the composition is such that the composition does not irritate the nasal cavity.

In some embodiments, the pharmaceutical composition further comprises one or more anti-microbial preservatives. Examples of preservatives include, but are not limited to, mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof. Preservatives may precipitate in the presence of other excipients in the composition. For example, benzalkonium chloride can precipitate. Thus, in some embodiments in which a preservative is present, the preservative is one that does not precipitate but remains in solution in the composition. A suitable preservative is phenylethyl alcohol. The one or more anti-microbial preservatives can be included, for example, to suppress microbial and fungal growth in the final delivery systems.

In some embodiments, the pharmaceutical composition further comprises one or more antioxidants. Suitable antioxidants may optionally be included in the nasal composition, for example, to stabilize the formulation against long term effects of oxidation. Examples of antioxidants include, but are not limited to, Vitamin E (and derivatives thereof), Vitamin C (and derivatives thereof), BHT, BHA, propyl gallate, citric acid, erythorbic acid, monothioglycerol, a metabisulfite (sodium or potassium), propionic acid, sodium sulfite, and thymol.

In some embodiments, the pharmaceutical composition further comprises one or more dose confirmation excipients, which help facilitate proper usage and/or avoid overdosage. For medications that are administered intranasally, it can be difficult for the subject to determine whether the medication has been properly administered. The inclusion of a dose confirmation excipient can provide positive feedback to the subject after administration, confirming that the dose has been administered intranasally. In some embodiments, the dose confirming excipient has an odor that can allow the subject to confirm that the dose was administered and taken or deposited into the nose. Other feedback mechanisms can be used to confirm that the dose has been administered appropriately. Odor is one non limiting example. In some embodiments, the dose confirmation excipient is phenylethyl alcohol. Without being bound by theory, dose confirmation excipients provide sensory feedback to the patient to confirm that a dose has been delivered, thereby increasing compliance with the prescribed dosing regimen and reducing the potential for overdosing. Phenylethyl alcohol has a distinct odor and may serve as both an antimicrobial and dose confirmation excipient in the compositions previously described.

In some embodiments, the pharmaceutical composition further comprises one or more humectants. Examples of humectants include, but are not limited to, glycerin, propylene glycol, polyethylene glycol, and a sugar/sugar alcohol, or any combination thereof. Humectants can provide moisturizing effects and reduce nasal irritation.

In some embodiments, the pharmaceutical composition further comprises one or more osmolality adjusting agents. The osmality of the intranasal composition can also be relevant to the uptake of the medication intranasally. Suitable osmolality adjusting agents include, but not limited to, sodium chloride, dextrose, sugars, or any combination thereof. The osmolality adjusting agents can also be included in the composition to produce solutions that are less irritating to the nasal mucosa by aligning the osmolality of the administered solution with the nasal mucosa.

In some embodiments, the pharmaceutical composition is free of a viscosity enhancing agent. Viscosity enhancing agents including, but not limited to, Methocel E4M can optionally be added to increase residence time of the instilled or spray solution with the nasal mucosa. However, in the case of dexmedetomidine, the use of a viscosity increasing agent may result in diminished dexmedetomidine plasma levels and may therefore be omitted under certain conditions, such as when the dexmedetomidine composition is intended for rapid uptake. Therefore, it was surprisingly found that the viscosity of the intranasal composition can affect the uptake of the active ingredient. Thus, in some embodiments, an increase in viscosity can decrease the uptake of dexmedetomidine. Accordingly, in some embodiments, the composition is free of a polymer that increases the viscosity of a liquid vehicle or composition. In some embodiments, the polymer is a water-soluble polymer. Examples of a soluble polymer include, but are not limited to, a cellulose ether (e.g. hydroxypropyl methylcellulose), other cellulose based polymers (methylcellulose, hydroxyethyl cellulose, hydroxypropyl cellulose, etc.), povidone, polyvinyl alcohol, gums (e.g. xanthum gum), polyethylene glycol (PEG), polyethylene oxide (PEO), hyaluronic acid (and derivates and salts thereof), carrageenan, dextran, and poloxamer. In some embodiments, the cellulose ether is hydroxypropyl methylcellulose (HPMC). Thus, in some embodiments, the composition is free of HPMC. In some embodiments, the viscosity of the intranasal composition is no greater than the viscosity of water.

In some embodiments, the viscosity of the intranasal composition is no greater than 110%, no greater than 120%, no greater than 130%, no greater than 140%, no greater than 150%, no greater than 160%, no greater than 170%, no greater than 180%, no greater than 190%, or no greater than 200% of the viscosity of water. In some embodiments, the viscosity of the intranasal formulation is about 1 mPa*s, 2 mPa*s, 3 mPa*s, 4 mPa*s, or 5 mPa*s. In some embodiments, the viscosity of the intranasal formulation is less than about 1 mPa*s, 2 mPa*s, 3 mPa*s, 4 mPa*s, or 5 mPa*s. In some embodiments, the viscosity of the intranasal formulation is from about 1 mPa*s to about 2 mPa*s, from about 1 mPa*s to about 3 mPa*s, from about 1 mPa*s to about 4 mPa*s, from about 1 mPa*s to about 5 mPa*s, from about 1.5 mPa*s to about 2.5 mPa*s, from about 2 mPa*s to about 3 mPa*s, from about 2 mPa*s to about 4 mPa*s, or from about 2 mPa*s to about 5 mPa*s.

The viscosity of a composition can be calculated by various methods. The viscosity can also be directly measured using various techniques. For example, the viscosity of a composition can be calculated according to the following equation. The equation expresses the illustrated approximate relationship between solution viscosity and polymer concentration is $\eta^{1/8}=(C^*\alpha)+1$, where $\eta$ is the solution viscosity in millipascal-seconds, C is the polymer concentration in solution (expressed in percent), and α is a constant specific to the molecular weight. For example, the value of α can be calculated by substitution and may then be used to calculate the approximate viscosity at the desired concentration.

It is also known in the art that the compounds and compositions comprising the same can be contained in formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. In some embodiments, the compounds and compositions comprising the same can be contained in formulations that do not comprise pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. In some embodiments, the compounds and compositions comprising the same can be contained in formulations that do not comprise a surfactant. The pharmaceutical compositions can also comprise suitable solid or gel phase carriers or excipients. In addition to other excipients described herein, examples of such carriers or excipients include, but are not limited to, calcium carbonate, calcium phosphate, various sugars, starches, cellulose derivatives, gelatin, and polymers such as polyethylene glycols. In some embodiments, the compounds described herein can be used with agents including, but not limited to, topical analgesics (e.g., lidocaine), barrier devices (e.g., GelClair), or rinses (e.g., Caphosol).

In some embodiments, when administered to a human, the compounds can be sterile. Water can be a suitable carrier when the compound is administered intranasally. Saline solutions and aqueous dextrose and glycerol solutions can also be employed as liquid carriers. Suitable pharmaceutical carriers also include excipients such as, but not limited to, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions described herein can take the form of a solution, suspension, emulsion, powder, sustained-release formulation, aerosol, spray, or any other form suitable for the uses described herein. Examples of suitable pharmaceutical carriers are described in Remington's Pharmaceutical Sciences, A. R. Gennaro (Editor) Mack Publishing Co.

In some embodiments, the compounds are formulated in accordance with routine procedures as a pharmaceutical composition adapted for administration to humans. In some embodiments, compounds are solutions in sterile isotonic aqueous buffer and, for example, with the other components described herein. Where necessary, the compositions can also include a solubilizing agent. Compositions may optionally include a local anesthetic such as lidocaine to ease pain at the site of the administration that can be due to, for example, irritation from the composition.

In some embodiments, the present invention also provides pharmaceutical packs or kits comprising one or more containers containing one or more compounds described herein. Optionally associated with such container(s) can be a notice in the form prescribed by a governmental agency regulating the manufacture, use or sale of pharmaceuticals or biological products, which notice reflects approval by the agency of manufacture, use or sale for human administration for treating a condition, disease, or disorder described herein. In some embodiments, the kit contains more than one compound described herein. In some embodiments, the kit comprises a compound described herein in a single unit dosage form, such as a single dose within an intranasal administrable device such as a metered dose device that administers a spray or a powder to a nasal activity.

In some embodiments, the components described herein are supplied either separately or mixed together in unit dosage form, for example, the components can be combined to create an intranasal formulation. Examples of making the formulations are described herein and can be modified to yield any suitable intranasal formulation.

The pharmaceutical compositions can be in unit dosage form. In such form, the composition can be divided into unit doses containing appropriate quantities of the active component. The unit dosage form can be a packaged preparation, the package containing discrete quantities of the preparations. The dosage form can be any form including, but not limited to, the forms described herein.

In some embodiments, a composition of the present invention is in the form of a liquid wherein the active agent is present in solution, in suspension, as an emulsion, or as a solution/suspension. In some embodiments, the liquid composition is in the form of a gel. In other embodiments, the liquid composition is aqueous. In other embodiments, the composition is in the form of an ointment. The liquid composition can also be a spray.

The liquid vehicle refers to the liquid in which dexmedetomidine is suspended or dissolved. Examples of the liquid vehicles include, but are not limited to, water, saline, an aqueous solution, DMSO, and the like.

In some embodiments, the pharmaceutical composition comprises, in addition to dexmedetomidine, the following (all based on % w/w): about 0.245% anhydrous sodium citrate, about 0.01% anhydrous citric acid, about 0.7% sodium chloride, about 99.045% purified water, at an initial pH of 6.31 adjusted to a final pH of about 6.78 with 2N sodium hydroxide. In some embodiments, the pharmaceutical composition comprises, in addition to dexmedetomidine, the following (all based on % w/w): about 0.245% anhydrous sodium citrate, about 0.01% anhydrous citric acid, about 0.1% Methocel E4M, about 0.7% sodium chloride, about 98.945% purified water, at an initial pH of 6.36 adjusted to a final pH of about 6.83 with 2N sodium hydroxide. In some embodiments, the pharmaceutical composition comprises, in addition to dexmedetomidine, the following (all based on % w/w): about 0.193% sodium phosphate monobasic (monohydrate), about 0.162% sodium phosphate dibasic (heptahydrate), about 0.7% sodium chloride, about 98.946% purified water, at an initial pH of 6.37 adjusted to a final pH of about 6.53 with 2N sodium hydroxide. In some embodiments, the pharmaceutical composition comprises, in addition to dexmedetomidine, the following (all based on % w/w): about 0.193% sodium phosphate monobasic (monohydrate), about 0.162% sodium phosphate dibasic (heptahydrate), about 0.75% sodium chloride, about 98.896% purified water, at an initial pH of 6.37 adjusted to a final pH of about 6.53 with 2N sodium hydroxide. In some embodiments, the pharmaceutical composition comprises, in addition to dexmedetomidine, the following (all based on % w/w): about 0.193% sodium phosphate monobasic (monohydrate), about 0.162% sodium phosphate dibasic (heptahydrate), about 0.25% phenylethyl alcohol, about 0.68% sodium chloride, about 98.616% purified water, at an initial pH of 6.15 adjusted to a final pH of about 6.51 with 2N sodium hydroxide. In some embodiments, the pharmaceutical composition comprises, in addition to dexmedetomidine, the following (all based on % w/w): about 0.226% anhydrous sodium citrate, about 0.024% anhydrous citric acid, about 0.25% phenylethyl alcohol, about 0.76% sodium chloride, about 98.64% purified water, at an initial pH of 5.68 adjusted to a final pH of about 6.04 with 2N sodium hydroxide.

The compositions comprising dexmedetomidine described herein are stable. For a 0.035% dexmedetomidine hydrochloride intranasal spray formulation, for example, the stability is at least 3 months, at least 6 months, at least 9 months, or at least one year wherein the storage conditions are 25° C. at 60% relative humidity, and at least 1 month, at least 3 months, at least 6 months wherein the storage conditions are 40° C. at 75% relative humidity.

Where dexmedetomidine, or a pharmaceutically acceptable salt thereof, is used in any method or device described herein, it is understood that any and all metabolites of dexmedetomidine, or a pharmaceutically acceptable salt thereof, can also be used likewise.

In order that the invention disclosed herein may be more efficiently understood, examples are provided below. It should be understood that these examples are for illustrative purposes only and are not to be construed as limiting the invention in any manner.

EXAMPLES

Example 1: Preparation of Intranasal Formulations

To a container, purified water, USP was added. To the water, anhydrous citric acid, sodium citrate dihydrate, sodium chloride, phenylethyl alcohol, and disodium EDTA was mixed until dissolved. The pH of the solution was modified, if necessary, to be in the range of 6.0 and 6.5. With continued mixing, dexmedetomidine HCl was added until dissolved. Water was added to adjust the dexmedetomidine HCl to a final selected concentration.

Example 2: Intranasal Formulations of Dexmedetomidine

Nasal delivery of dexmedetomidine HCl (DEX) was evaluated from aqueous sprays to provide pharmacokinetic profiles that provide analgesia without significant sedation. The nasal route of delivery is often desired by patients in pain that may be unable or unwilling to tolerate the treatment by an oral route (e.g., buccal, sublingual, swallowing), by a rectal route (e.g. foams, suppositories, etc.), or an injection route. In addition to the aqueous nasal sprays initially developed for evaluation of intranasally administered DEX, the formulations can be modified to include dry powders, suspensions, and/or vapors as would be apparent from the description contained herein.

An initial screening of DEX aqueous nasal compositions administered as nasal drops was evaluated in a canine model. The influence of buffer species and viscosity was evaluated in the following base compositions.

| Component | First Placebo Base Composition (% w/w) | | |
|---|---|---|---|
| | Formulation 1 | Formulation 2 | Formulation 3 |
| Sodium Citrate, Anhydrous | 0.245 | 0.245 | — |
| Citric Acid, Anhydrous | 0.010 | 0.010 | — |
| Methocel E4M | — | 0.100 | — |
| Sodium Phosphate Monobasic, Monohydrate | — | — | 0.193 |
| Sodium Phosphate Dibasic, Heptahydrate | — | — | 0.162 |
| Sodium Chloride | 0.700 | 0.700 | 0.700 |
| Purified Water | 99.045 | 98.945 | 98.946 |
| Total | 100.000 | 100.000 | 100.000 |
| Initial pH | 6.31 | 6.36 | 6.37 |
| Final pH[1] | 6.78 | 6.83 | 6.53 |

[1]Adjusted with 2N Sodium Hydroxide.

DEX was dissolved into the Placebo Base Compositions to prepare Formulation solutions that would deliver 50 μg DEX in 100 μL volume. The DEX compositions were expressed as follows.

| Component | DEX Nasal Drop Composition (% w/v) | | |
|---|---|---|---|
| | Formulation 1-DEX | Formulation 2-DEX | Formulation 3-DEX |
| Dexmedetomidine HCl | 0.059 | 0.059 | 0.059 |
| Formulation 1 | 99.941 | — | — |
| Formulation 2 | — | 99.941 | — |
| Formulation 3 | — | — | 99.941 |
| Total | 100.000 | 100.000 | 100.000 |

The density of the DEX nasal drop compositions was approximately 1 g/mL at room temperature and allowed for weight and volume to be used interchangeably. The three DEX Nasal Drop Compositions were administered to canines. Surprisingly, compositions without a cellulose ether, which is a viscosity enhancing agent, such as Formulation 1-Dex and Formulation 3-Dex, provided significant plasma levels in less than 15 minutes after administration. Also surprisingly, Formulation 2-Dex, which contained 0.1% Methocel E4M and had the highest solution viscosity, resulted in negligible plasma levels of DEX, indicating that increased solution viscosity diminished the effectiveness of DEX delivered intranasally. This result was unexpected.

The influence of additional formulation additives was further investigated from aqueous DEX solutions that were delivered as fine mists from multiple-use aqueous spray pumps. The following placebo base compositions were prepared.

| Component | Second Placebo Base Composition (% w/w) | | |
|---|---|---|---|
| | Formulation 4 | Formulation 5 | Formulation 6 |
| Sodium Citrate, Anhydrous | — | — | 0.226 |
| Citric Acid, Anhydrous | — | — | 0.024 |
| Sodium Phosphate Monobasic, Monohydrate | 0.193 | 0.193 | — |
| Sodium Phosphate Dibasic, Heptahydrate | 0.162 | 0.162 | — |
| Phenylethyl Alcohol | — | 0.250 | 0.250 |
| Disodium Edetate Dihydrate | — | 0.100 | 0.100 |

-continued

| Component | Second Placebo Base Composition (% w/w) | | |
|---|---|---|---|
| | Formulation 4 | Formulation 5 | Formulation 6 |
| Sodium Chloride | 0.750 | 0.680 | 0.760 |
| Purified Water | 98.896 | 98.616 | 98.640 |
| Total | 100.000 | 100.000 | 100.000 |
| Initial pH | 6.37 | 6.15 | 5.68 |
| Final pH[1] | 6.53 | 6.51 | 6.04 |

[1]Adjusted with 2N Sodium Hydroxide.

DEX was dissolved into the second set of Placebo Base Compositions to prepare solutions that would deliver 50 μg DEX in 100 μL volume. The DEX compositions are expressed as follows.

| Component | DEX Nasal Spray Composition (% w/v) | | |
|---|---|---|---|
| | Formulation 4-Dex | Formulation 5-Dex | Formulation 6-Dex |
| Dexmedetomidine HCl | 0.059 | 0.059 | 0.059 |
| Formulation 4 | 99.941 | — | — |
| Formulation 5 | — | 99.941 | — |
| Formulation 6 | — | — | 99.941 |
| Total | 100.000 | 100.000 | 100.000 |
| Calculated Osmolality (mOsm/kg) | 288 | 368 | 306 |

The density of the DEX nasal spray compositions was approximately 1 g/mL at room temperature and allowed for weight and volume to be used interchangeably. The three DEX Nasal Spray Compositions were administered to canines using a manually actuated nasal pump. The results of the canine study indicated measurable plasma levels as early as 5 minutes and decreasing plasma levels according to Formulation 4-Dex>Formulation 5-Dex>Formulation 6-Dex.

An additional placebo base composition was prepared as defined below.

| Component | Third Placebo Base Composition (% w/w) Formulation 7 |
|---|---|
| Sodium Citrate, Anhydrous | 0.230 |
| Citric Acid, Anhydrous | 0.020 |
| Phenylethyl Alcohol | 0.250 |
| Disodium Edetate Dihydrate | 0.100 |
| Sodium Chloride | 0.760 |
| Purified Water | 98.640 |
| Total | 100.000 |
| Initial pH | 5.79 |
| Final pH[1] | 6.27 |

[1]Adjusted with 2N Sodium Hydroxide.

DEX was dissolved into the third Placebo Base Composition to prepare a solution that would deliver 25 μg DEX in 100 μL volume. The DEX composition is expressed as follows.

| Component | DEX Nasal Spray Composition (% w/v) Formulation 7-Dex |
|---|---|
| Dexmedetomidine HCl | 0.0295 |
| Formulation 7 | 99.9705 |
| Total | 100.0000 |
| Final pH | 6.20 |

The density of the DEX nasal spray composition was approximately 1 g/mL at room temperature and allowed for weight and volume to be used interchangeably. The DEX nasal compositions were developed as an aqueous solution that could be delivered as nasal drops or as a fine mist from a nasal spray device. The DEX nasal compositions minimally contained DEX dissolved in purified water at a suitable concentration to deliver the intended DEX dose in 25 μL to 200 μL. Dose volumes less than 25 μL can result in variable delivery while dose volumes greater than 200 μL can result in excess run off from the nasal cavity. The aqueous nasal compositions can optionally contain additional materials to facilitate the intranasal delivery of DEX.

Example 3: Droplet Particle Size Determination

In vitro spray pump performance of the Drug Product (DEX-IN.02 50 μg API/100 μL Intranasal Spray and DEX-IN.03 25 μg API/50 μL Intranasal Spray) and Placebo (DEX-IN.02P 100 μL Intranasal Spray) was based on droplet size distribution as measured by laser diffraction using a Malvern Spraytec. The Malvern Spraytec operates based on a laser diffraction principle and is a commonly used technique to characterize droplet size distributions from nasal sprays. The droplet size distribution was characterized by the following metrics: volume distribution (Dv10, Dv50, Dv90), Span and percentage (%) less than 10 μm per the FDA CMC Guidance for Nasal Sprays (2002) and FDA Draft Guidance for Industry: Bioavailability and Bioequivalence Studies for Nasal Aerosols and Nasal Sprays for Local Action, April 2003.

Example 4: Pharmacokinetic Study of Dexmedetomidine Formulations Following Intranasal or Sublingual Administration in Dogs One objective of the present study was to compare the pharmacokinetics of multiple experimental dexmedetomidine formulations to the pharmacokinetics of a commercial formulation of dexmedetomidine when administered intranasally or sublingually in dogs. For each dosing event, five male dogs were dosed intranasally or sublingually with 50 μg of dexmedetomidine free-base (equivalent to 59 μg of dexmedetomidine HCl) in 100 μL of formulation, except for Formulation 7-Dex, where the dogs were dosed with 25 μg of dexmedetomidine free-base (equivalent to 29.5 μg of dexmedetomidine HCl) in 100 μL, and the PRECEDEX® formulation, which contained 50 μg dexmedetomidine base equivalent in 500 μL of solution. Dosing was performed in 10 dosing events in three segments with the formulations, with a minimum 2-day interval between the dosing events, as shown in the table below:

| Segment | Dosing Event | Formulation | Dose Route |
|---|---|---|---|
| 1 | 1 | Formulation 1-Dex* | Intranasal |
|   | 2 | Formulation 3-Dex* | Intranasal |
|   | 3 | Formulation 2-Dex* | Intranasal |
|   | 4 | PRECEDEX®* | Intranasal |
| 2 | 5 | Formulation 4-Dex* | Intranasal |
|   | 6 | Formulation 5-Dex* | Intranasal |
|   | 7 | Formulation 6-Dex* | Intranasal |
| 3 | 8** | Formulation 6-Dex* | Intranasal |
|   | 9 | Formulation 7-Dex*** | Intranasal |
|   | 10 | DEX-SL.01* | Sublingual |

*Dose = 50 µg of dexmedetomidine free-base (equiv. to 59 µg of dexmedetomidine HCl).
**Redose of Formulation 6-Dex using a new sprayer.
***Dose = 25 µg of dexmedetomidine free-base (equiv. to 29.5 µg of dexmedetomidine HCl).

Mean pharmacokinetic parameters for dexmedetomidine are summarized below.

| Formulation (Dosing Event) | $T_{max}$ (hr) | $t_{1/2}$ (hr) | $C_{max}$ (ng/ml) | $AUC_{last}$ (hr*ng/ml) | $AUC_{0-\infty}$ (hr*ng/ml) |
|---|---|---|---|---|---|
| Formulation 1-DEX (1) | 0.7 | 0.93 | 8.88 | 7.72 | 7.18 |
| Formulation 2-DEX (2) | 0.7 | NC1 | 16.9 | 12.3 | NC1 |
| Formulation 3-DEX (3) | 0.42 | 0.43 | 1.30 | 1.10 | 1.16 |
| PRECEDEX® (4) | 0.38 | 0.52 | 12.2 | 6.68 | 6.69 |
| Formulation 4-DEX (5) | 0.4 | 0.47 | 1.35 | 1.12 | 0.984 |
| Formulation 5-DEX (6) | 0.80 | 0.50 | 2.46 | 2.44 | 2.62 |
| Formulation 6-DEX (7) | 0.42 | 0.56 | 9.05 | 6.57 | 2.18 |
| Formulation 6-DEX (8)* | 0.27 | 0.79 | 5.92 | 3.61 | 6.06 |
| Formulation 7-DEX (9) | 0.32 | 0.63 | 1.33 | 1.18 | 1.09 |
| DEX-SL.01 (10) | 0.60 | 1.72 | 2.15 | 2.27 | 4.75 |

NC1 = Value could not be calculated by WinNonlin due to insufficient data points for the elimination phase.
*Redose of Formulation 6-DEX using a new sprayer.

For intranasal administration (dose events 1 to 9), $T_{max}$ and elimination half-life for dexmedetomidine were similar between the PRECEDEX® formulation and the experimental doses 1-3 and 5-9. The mean $T_{max}$ for dexmedetomidine for the PRECEDEX® formulation was 0.38 hours, and the mean $T_{max}$ for dexmedetomidine for the experimental formulations that were administered intranasally (doses 1-3, 5-9) ranged from 0.32 hours to 0.80 hours. The mean elimination half-life for dexmedetomidine for the PRECEDEX® formulation was 0.52 hours, and the mean elimination half-life for dexmedetomidine for the experimental formulations administered intranasally (doses 1-3, 5-9) ranged from 0.43 hours to 0.93 hours. For sublingual administration (dosing event 10, formulation DEX-SL.01), the mean $T_{max}$ was 0.60 hours similar to the $T_{max}$ obtained following intranasal administration of PRECEDEX® and experimental doses 1-9, while the mean elimination half-life for the DEX-SL.01 formulation was 1.72 hours, longer than the elimination half-life obtained following intranasal administration of PRECEDEX® and experimental doses 1-3 and 5-9.

Based on $C_{max}$ and $AUC_{last}$, dexmedetomidine exposure following intranasal administration was highest for the Formulation 3-DEX formulation. The mean $C_{max}$ for Formulation 3-DEX formulation was approximately 140% of the mean $C_{max}$ for PRECEDEX®, while mean $AUC_{last}$ for the Formulation 3-DEX formulation was approximately 180% of the mean $AUC_{last}$ for PRECEDEX®. The mean $AUC_{last}$ for the Formulation 6-Dex and Formulation 1-DEX formulations were similar to that of PRECEDEX®, while the mean $C_{max}$ for these formulations were approximately 70% of the mean $C_{max}$ for PRECEDEX®. The mean $C_{max}$ and $AUC_{last}$ for all other experimental formulations dosed intranasally were lower than that for PRECEDEX®. Dexmedetomidine exposure following intranasal administration was lowest for the Formulation 2-DEX and Formulation 7-DEX formulations. Surprisingly, dexmedetomidine exposure following sublingual administration of formulation DEX-SL.01 was substantially lower than for intranasal administration of PRECEDEX®; the mean $C_{max}$ for the DEX-SL.01 formulation was 18% of the mean $C_{max}$ for PRECEDEX®, and mean $AUC_{last}$ for the DEX-SL.01 formulation was 34% of the mean $AUC_{last}$ for PRECEDEX®.

| Formulation (Dosing Event) | $T_{max}$ (far) | $t_{1/2}$ (hr) | $C_{max}$ (ng/mL) | $AUC_{last}$ (hr*ng/mL) | $AUC_{0-\infty}$ (hr*ng/mL) |
|---|---|---|---|---|---|
| Formulation 1-DEX (1) | 1.75 | NC[1] | 0.272 | 0.355 | NC[1] |
| Formulation 2-DEX (2) | 1.80 | NC[1] | 0.291 | 0.386 | NC[1] |
| Formulation 3-DEX (3) | 0.65 | NC[1] | 0.285 | 0.203 | NC[1] |
| PRECEDEX® (4) | 1.55 | NC[1] | 0.248 | 0.358 | NC[1] |
| Formulation 4-DEX (5) | 1.00 | NC[1] | 0.0847 | 0.111 | NC[1] |
| Formulation 5-DEX (6) | 1.35 | 1.28 | 0.116 | 0.169 | 0.233 |
| Formulation 6-DEX (7) | 0.90 | NC[1] | 0.221 | 0.319 | NC[1] |
| Formulation 6-DEX (8)* | 1.15 | 7.29 | 0.168 | 0.265 | 2.38 |
| Formulation 7-DEX (9) | 1.25 | 8.70 | 0.0999 | 0.109 | 1.15 |
| DEX-SL.01 (10) | 1.80 | NC[1] | 0.152 | 0.204 | NC[1] |

NC[1] = Value could not be calculated by WinNonlin due to insufficient data points for the elimination phase.
*Redose of Formulation 6-Dex using a sprayer.

For intranasal administration (dose events 1 to 9), the $T_{max}$ for this table was generally similar between the PRECEDEX® formulation and the experimental doses 1-3 and 5-9. The mean $T_{max}$ for the PRECEDEX® formulation was 1.55 hours, and the mean $T_{max}$ for the experimental formulations administered intranasally (doses 1-3, 5-9) ranged from 0.65 hours to 1.80 hours. For most formulations, the elimination half-life was either not calculated or not reported due to insufficient data points for the elimination phase or poor goodness-of-fit (R2<0.8) for the elimination phase. Where calculable, the half-life ranged from 1.3 hours to 8.7 hours. For sublingual administration (dosing event 10, formulation DEX-SL.01), the mean $T_{max}$ was 1.80 hours, similar to the $T_{max}$ obtained following intranasal administration of PRECEDEX® and the experimental doses 1-3 and 5-9.

Based on $C_{max}$ and $AUC_{last}$, exposure following intranasal administration was highest for the Formulation 3-Dex formulation. The mean $C_{max}$ for the Formulation 3-Dex formulation was approximately 117% of the mean $C_{max}$ for PRECEDEX®, while the mean $AUC_{last}$ for the Formulation 3-Dex formulation was approximately 108% of the mean $AUC_{last}$ for PRECEDEX®. Mean $C_{max}$ and $AUC_{last}$ for all other experimental formulations dosed intranasally were similar to that for PRECEDEX®, except for Formulation 4-DEX and Formulation 7-DEX (the amount of dexmedetomidine dosed with Formulation 7-DEX was half that of the other formulations). Exposure following sublingual administration of formulation DEX-SL.01 was lower than for intranasal administration of PRECEDEX®; mean $C_{max}$ for the DEX-SL.01 formulation was approximately 61% of the mean $C_{max}$ for PRECEDEX®, and mean $AUC_{last}$ for the DEX-SL.01 formulation was approximately 57% of the mean $AUC_{last}$ for PRECEDEX®.

The results presented herein, surprisingly show that when compared to the previously studied sublingually administered formulation DEX-SL.01, absorption occurs more quickly via the nasal route. Therefore, intranasal administration of DEX surprisingly may provide faster pain relief and/or prevention of pain in subjects as compared to sublingual or methods of administering DEX across the oral mucosa, without significant sedation, and with little or no effect on blood pressure.

Dosing

Doses 1-3 were administered intranasally with a micropipette with the head inverted for dosing. The dosage was 50 μg of dexmedetomidine free-base (equivalent to 59 μg of dexmedetomidine HCl) in 100 μL of formulation. Dose 4 was administered using a commercial nasal spray bottle. Spray doses were administered with the head upright, alternating nostrils for each spray. The head was inverted for 30 seconds to 1 minute after spray administration. The spray bottle administers 100 μL per spray, and five sprays were required to deliver the dosage of 50 μg of dexmedetomidine free-base (equivalent to 59 μg of dexmedetomidine HCl). The spray bottle was primed in an area remote from dosing prior to dose administration to prevent possible cross-contamination. Additionally, dosing was performed in an area remote from blood collection to prevent possible contamination of blood samples with aerosolized test article.

Doses 5-7 were administered using a commercial nasal spray bottle. Spray doses were administered with the head upright. The head was inverted for 30 seconds to 1 minute after spray administration. The spray bottle administers 100 μL per spray, and one spray was required to deliver the dosage of 50 μg of dexmedetomidine free base (equivalent to 59 μg of dexmedetomidine HCl). The spray bottle was primed using five spray actuations in an area remote from dosing prior to dose administration to prevent possible cross-contamination. Additionally, dosing was performed in an area remote from blood collection to prevent possible contamination of blood samples with aerosolized test article.

Dose 8 was administered using a commercial nasal spray bottle. Spray doses were administered with the head upright. The head was inverted for 30 seconds to 1 minute after spray administration. The spray bottle administered 100 μL per spray, and one spray was required to deliver the dosage of 50 μg of dexmedetomidine free base (equivalent to 59 μg of dexmedetomidine HCl). The spray bottle was primed using five spray actuations in an area remote from dosing prior to dose administration to prevent possible cross-contamination. Additionally, dosing was performed in an area remote from blood collection to prevent possible contamination of blood samples with aerosolized test article.

Dose 9 was administered using a commercial nasal spray bottle. Spray doses were administered with the head upright. The head was inverted for 30 seconds to 1 minute after spray administration. The spray bottle administered 100 μL per spray, and one spray was required to deliver the dosage of 25 μg of dexmedetomidine free base (equivalent to 29.5 μg of dexmedetomidine HCl). The spray bottle was primed using five spray actuations in an area remote from dosing prior to dose administration to prevent possible cross-contamination. Additionally, dosing was performed in an area remote from blood collection to prevent possible contamination of blood samples with aerosolized test article.

Dose 10 was administered sublingually with a micropipette. The dosage was 50 μg of dexmedetomidine free base (equivalent to 59 μg of dexmedetomidine HCl) in 100 μL of formulation.

For intranasal administrations, the formulations were administered intranasally. Following dosing, the dog's nares were held shut and the head inverted for approximately 1 minute. Each dosing event was separated by a minimum of 2 days to allow an appropriate washout.

After dosing, blood samples were obtained and tested for DEX plasma levels.

Example 5: Pharmacokinetics of Intranasally Administered Dexmedetomidine in Humans Four different formulations of DEX were used. PRECEDEX® (Treatment A) at a dose of 25 μg which was administered intravenously over 10 minutes and 3 different intranasal dosages or formulations. Formulation B (35 μg administered in 100 μl in one nostril via 1 spray); Formulation C (35 μg total administered via 2 nostrils); and Formulation D (17.5 μg administered in 50 μl in one nostril via 1 spray).

|  | Treatment A Precedex IV 25 μg | Treatment B DEX-IN.01 35 μg 100 μl in one nostril | Treatment C DEX-IN.01 35 μg 50 μl in each nostril | Treatment D DEX-IN.01 17.5 μg 50 μl in one nostril |
|---|---|---|---|---|
| $C_{max}$ (ng/ml) | 0.61 (58.7%) | 0.17 (21.7%) | 0.14 (34.0%) | 0.08 (31.9%) |
| $AUC_{0-24}$ (hr ng/ml) | 0.71 (27.7%) | 0.83 (23.6%) | 0.75 (22.5%) | 0.38 (16.6%) |
| $T_{max}$ (hrs) | 0.17 (0.17, 0.25) | 1.00 (0.33, 4.00)† | 1.25 (0.33, 4.00) | 1.13 (0.33, 2.00) |
| $t_{1/2}$ (hrs) | 2.04 ± 0.200‡ | 2.43 ± 0.825§ | 2.64 ± 0.777§ | 1.60 (NA)¥ |

[1] Geometric means (CV %) for $C_{max}$ and $AUC_{0-24}$ median (min, max) for $T_{max}$; and arithmetic mean ± SD for $t_{1/2}$;
†n = 11;
‡n = 10;
§n = 4;
¥n = 1

The pharmacokinetics observed showed the surprising result that the administration of the dose in single spray to a single nostril (Treatment B) provided a better $C_{max}$ and a shorter $T_{max}$ as compared to the same total dose administered in two nostrils via 2 sprays (half the dose being administered into each nostril). This result could not have been predicted and is opposite of what would have been expected by the skilled artisan, in part, due to a surface area comparison. The mean plasma concentrations produced by Treatment B reached a minimum target concentration (0.1 ng/ml) within 20 minutes after dosing. This surprising result of administering to a single nostril can facilitate the more rapid onset of activity (e.g., pain relief) in target patient populations. The rate of absorption observed in Treatment B was more rapid than previously studied non-IV formulations or routes of administration. This unexpected more rapid absorption can allow for the fast onset of analgesic effects. In fact, the analgesic effects can begin in less than 20 minutes. Plasma concentrations achieved with the 17.5 and 35 µg intranasal administration are provided in FIG. 1.

Dosing

Healthy volunteers were administered the selected dose intranasally or, if indicated, another route of administration. A single nostril was administered to at a time with the untreated nostril covered by a finger. Blood samples were taken and measured for DEX concentrations as indicated.

Example 6: Phase 1, Two Period, Open Label, Multiple-Dose Evaluation of the Safety, Tolerability, and Pharmacokinetics of Intranasal Dexmedetomidine in Healthy Volunteers The primary objective of this study was to evaluate the pharmacokinetic profile of multiple doses of intranasal dexmedetomidine in healthy male and female subjects. Secondary endpoints of this study were to evaluate the safety and tolerability of intranasal dexmedetomidine in healthy volunteers.

Methodology

This was a Phase 1, open-label, two period, repeated dose study in healthy subjects to investigate the safety, tolerability, and pharmacokinetics of intranasal dexmedetomidine. A total of 12 subjects (6 male and 6 female) were planned and enrolled. Healthy subjects between the ages of 18 and 50 years, inclusive, were screened for participation at one study site in the United States within 28 days before study drug administration. Medical history, physical examination, baseline laboratory testing, 12 lead electrocardiogram (ECG), pregnancy testing, vital sign measurements, and informed consent were completed during the screening visit.

All study doses were a 35 µg dose of DEX IN.01 administered as a single 100 µL spray into the left nostril. DEX-IN.01 contained 35 µg dexmedetomidine in each 100 µL of solution, as well as excipients including: citric acid, sodium citrate, sodium chloride, phenylethyl alcohol, disodium EDTA, and purified water. Doses of DEX-IN.01 utilized a 100 µL spray nozzle for administration into the nostril according to the treatment assignment.

During Period 1, subjects received two doses of study medication, separated by six hours. During Period 2, study participants received seven doses of study medication administered at six hour intervals. Study Periods were separated by not less than 24 hours between the last dose in Period 1 and the first dose in Period 2.

During Period 1, subjects were confined from the evening before dosing (Day −1) to approximately 18 hours after Dose 2 (Day 2). During Period 2, subjects were confined from the evening before dosing (Day −1) to approximately 24 hours after the last study dose (Day 3). While confined, subjects received a standardized daily diet.

Serial blood samples were collected at defined intervals during each study period in order to evaluate the pharmacokinetic properties of intranasally administered dexmedetomidine, and its metabolite. Whole blood was collected in 6 mL evacuated collection tubes treated with $K_2EDTA$.

Plasma samples were to be collected within ±2 minutes of the scheduled post-dose time through 60 minutes after dosing, samples collected 75 minutes to 6 hours after dosing were able to be collected within ±5 minutes, and samples collected at and beyond 12 hours after dosing were able to be collected within ±15 minutes of scheduled post-dose time. Actual times were to be recorded for all events, and any deviation outside the specified ranges were required to be clearly documented in the subject's study records.

Immediately after the collection of each sample, the collection tube was to be gently inverted and then placed in wet ice. Within 30 minutes of withdrawal, the tubes were centrifuged at about 2,000× gravity for 10-15 minutes to separate the cells from the plasma. No aids for separation were to be used. Two aliquots (≥0.5 mL each) of plasma were transferred from each sample with clean pipettes and placed in 2 polypropylene storage tubes in equal volumes. The storage tubes were labeled with the following information: protocol number, subject number, study day and relative time of sample (e.g., Period 1, Dose 1, 10 Minutes after dosing), and biologic matrix to be analyzed (e.g., plasma). Within 60 minutes of the collection time, the storage tubes were to be placed into a freezer at −20° C. or below; they remained in the freezer until shipment for analysis.

For pharmacokinetic analyses in Period 1, up to 12 blood samples were collected from each subject prior to and following administration of each study dose. These were collected at predose (Time 0) and at the following approximate times after each dose of study medication: 10, 20, 30, 45, 60, and 90 minutes and 2 and 4 hours; additional blood samples were collected at 6, 12 and 18 hours after Dose 2. In Period 2, up to 13 blood samples were collected from each subject prior to and following administration of Dose 1 and Dose 7. These were collected at predose (Time 0) and at the following approximate times after dosing with study medication: 10, 20, 30, 45, 60, and 90 minutes and 2 and 4 hours; additional blood samples were collected at 6, 12, 18 and 24 hours after Dose 7. Blood samples for Dose 2 through Dose 6 were collected at predose (Time 0) only.

A summary table of study visits, and the assigned time points, is provided for the overall study, Period 1, Period 2 Doses 1 and 7, and Period 2 Doses 2 through 6 in the table below.

TABLE

Summary of Study Visits

| | Period 1 | | | | | Period 2 | | | | | | | |
|---|---|---|---|---|---|---|---|---|---|---|---|---|---|
| | | Day 1 (hr) | | | | | Day 1 (hr) | | | Day 2 (hr) | | | Day 3 (hr) |
| Study Event | Day −1 | 0 | 6 | 24 | | Day −1 | 0 | 6 | 12 | 18 | 24 | 30 | 36 | 60 |
| Confinement | <----------X----------> | | | | Washout | <---------------------------X---------------------------> | | | | | | | |
| Study Dosing | | X | X | | | | X | X | X | X | X | X | X |

Inclusion Criteria:

Subjects met the following criteria to participate in the study: 1) was a man or woman between 18 and 50 years of age, inclusive; 2) for female subjects of childbearing potential, be surgically sterile, use double-barrier contraception, practice abstinence (must agree to use double-barrier contraception in the event of sexual activity) or using an insertable, injectable, transdermal, or combination oral contraceptive approved by the FDA through completion of the study and have negative results on a serum pregnancy test done before administration of study medication, and have negative results on subsequent urine pregnancy tests (women who are postmenopausal [no menses for at least 2 years] are also eligible to participate); 3) had a body mass index (BMI)≤32 kg/m$^2$ and a body weight between 50 and 95 kg, inclusive; and 4) was able to understand the study procedures, agree to participate in the study program, and voluntarily provide written informed consent.

Treatments Administered

Study personnel administered all doses of study medication according to the treatment schedule. Doses of dexmedetomidine were administered using the intranasal delivery device into the left nostril. Doses were administered into the assigned nostril with the untreated nostril covered with a finger. The subject's head was held in an upright position with the spray applicator inserted approximately ½" into the treated nostril. The subject inhaled through the treated nostril as the pump was squeezed and the dose was delivered.

After administration of study medication, participants were allowed to move around the study facility, and perform non-strenuous activities. Subjects may have been required to remain seated for a period of time by the study investigator if it was deemed unsafe for the subject to move around the study site without the accompaniment of study personnel.

Doses were subsequently evaluated in a single dose study in healthy volunteers where DEX-IN was evaluated using single and paired spray administration at doses of 17.5 and 35 μg. Based on the observed pharmacokinetics, it was determined that the 35 μg dose level administered into a single nostril would be most appropriate to explore further to achieve the targeted plasma concentrations. Plasma concentrations achieved with the 17.5 and 35 μg intranasal doses are provided in FIG. 1.

Ramsay Sedation Scale

The investigator, or designee, used the Ramsay Sedation Scale to assess each subject's degree of sedation. For each subject at each time point, the degree of sedation was assessed according to the Ramsay rating categories. The Ramsay Sedation Scale was performed pre-dose (Time 0), and at 30, 60 and 90 minutes after each study dose. All scores returned to their baseline level (Score 2) within six hours after dosing. Although an RSS score of 5 was assigned to two subjects during the course of the study, the majority of subjects did not experience significant sedation. Subjects were administered study doses every six hours, and completed safety monitoring activities subsequent to each dose, around the clock for seven doses during Period 2; the confounding effect of this schedule is not addressed in the assessment tool/results.

Criteria for Evaluation:

Pharmacokinetic parameters for the concentrations of dexmedetomidine and its major metabolite (ORM-14305) in plasma were calculated for Dose 1 and 2 during Period 1, and for Dose 1 and 7 during Period 2. The calculated parameters included peak (maximum) observed plasma drug concentration ($C_{max}$), time to $C_{max}$ ($T_{max}$), area under the concentration time curve (AUC) from Time 0 to last sampling time (t) with a quantifiable plasma drug concentration ($AUC_{0-t}$), AUC from Time 0 to 6 hours after dosing ($AUC_{0-6}$), AUC from Time 0 to infinity ($AUC_{0-\infty}$, for Period 1 Dose 2, and Period 2 Dose 7), and terminal phase elimination half life (VA, for Period 1 Dose 2, and Period 2 Dose 7).

Results:

Observed pharmacokinetic parameters, $C_{max}$, $T_{max}$, and $AUC_{0-6}$ of dexmedetomidine are presented in the table below.

Pharmacokinetic Parameters of Dexmedetomidine

| Parameters [1] | Period 1 Dose 1 | Period 1 Dose 2 | Period 2 Dose 1 | Period 2 Dose 7 |
|---|---|---|---|---|
| $C_{max}$ (ng/mL) | 0.09 (30.6)† | 0.16 (22.8)† | 0.12 (35.8)‡ | 0.13 (31.3)‡ |
| $T_{max}$ (hrs) | 1.26 (0.33, 4.00)† | 0.88 (0.33, 2.02)† | 1.01 (0.50, 2.00)‡ | 1.50 (0.33, 2.00)‡ |
| $AUC_{0-6}$ | 0.39 (31.7)† | 0.61 (19.2)† | 0.47 (32.6)‡ | 0.50 (31.1)‡ |
| $AUC_{last}$ (hr · ng/mL) | 0.38 (35.2)† | 0.63 (22.2)† | 0.47 (32.6)‡ | 0.51 (55.0)‡ |

[1] Geometric means (CV %) for $C_{max}$, $AUC_{0-6}$, and $AUC_{last}$; median (min, mix) for $T_{max}$
†n = 12;
‡n = 10

Comparison of Pharmacokinetic Parameters Between Doses

| Doses | $C_{max}$ (ng/mL) | $AUC_{last}$ (hr · ng/mL) | $AUC_{0-6}$ (hr · ng/mL) |
|---|---|---|---|
| Period 1 Dose 2: Period 1 Dose 1 | 164.1 (138.0, 195.0) | 164.2 (134.1, 201.0) | 156.9 (134.7, 182.8) |
| Period 2 Dose 7: Period 2 Dose 1 | 106.3 (82.5, 136.9) | 108.4 (77.8, 151.0) | 105.5 (81.1, 137.3) |
| Period 2 Dose 1: Period 1 Dose 1 | 127.7 (112.4, 145.2) | 125.1 (105.4, 148.6) | 122.8 (106.5, 141.7) |
| Period 2 Dose 7: Period 1 Dose 2 | 86.8 (71.0, 106.1) | 84.4 (66.5, 107.2) | 85.2 (72.0, 100.9) |

Data presented is Ratio % (90% CI)

Observed Mean Dexmedetomidine Plasma
Concentrations (ng/mL)

| Time Post-Dose | Period 1 (N = 12) | | Period 2 (N = 10) | |
|---|---|---|---|---|
| | Dose 1 | Dose 2 | Dose 1 | Dose 7 |
| 0 min | 0 | 0.033 ± 0.014 | 0 | 0.037 ± 0.016 |
| 10 min | 0.008 ± 0.014 | 0.077 ± 0.033 | 0.028 ± 0.035 | 0.059 ± 0.028 |
| 20 min | 0.060 ± 0.028 | 0.118 ± 0.054 | 0.073 ± 0.050 | 0.091 ± 0.033 |
| 30 min | 0.059 ± 0.020 | 0.134 ± 0.044 | 0.085 ± 0.041 | 0.101 ± 0.034 |
| 45 min | 0.083 ± 0.028 | 0.145 ± 0.040 | 0.112 ± 0.046 | 0.113 ± 0.032 |
| 60 min | 0.088 ± 0.024 | 0.145 ± 0.023 | 0.116 ± 0.041 | 0.119 ± 0.031 |
| 90 min | 0.090 ± 0.025 | 0.134 ± 0.014 | 0.116 ± 0.036 | 0.119 ± 0.031 |
| 2 hrs | 0.092 ± 0.026 | 0.135 ± 0.019 | 0.117 ± 0.039 | 0.126 ± 0.033 |
| 4 hrs | 0.067 ± 0.024 | 0.090 ± 0.023 | 0.073 ± 0.026 | 0.072 ± 0.072 |
| 6 hrs | 0.036 ± 0.010 | 0.050 ± 0.018 | 0.037 ± 0.012 | 0.048 ± 0.013 |
| 12 hrs | | 0.022 ± 0 | | 0.024 ± 0 |
| 18 hrs | | 0 | | 0 |
| 24 hrs | | | | 0 |

Observed Mean ORM-14305 Plasma
Concentrations (ng/mL)

| Time Post-Dose | Period 1 (N = 12) | | Period 2 (N = 10) | |
|---|---|---|---|---|
| | Dose 1 | Dose 2 | Dose 1 | Dose 7 |
| 0 min | 0 | 0.032 ± 0.019 | 0 | 0.085 ± 0.037 |
| 10 min | 0 | 0.032 ± 0.019 | 0 | 0.085 ± 0.036 |
| 20 min | 0 | 0.035 ± 0.015 | 0 | 0.083 ± 0.036 |
| 30 min | 0 | 0.042 ± 0.013 | 0 | 0.081 ± 0.032 |
| 45 min | 0 | 0.039 ± 0.014 | 0 | 0.078 ± 0.029 |
| 60 min | 0 | 0.042 ± 0.013 | 0 | 0.084 ± 0.034 |
| 90 min | 0 | 0.045 ± 0.014 | 0.002 ± 0.006 | 0.080 ± 0.034 |
| 2 hrs | 0.010 ± 0.013 | 0.053 ± 0.014 | 0.017 ± 0.015 | 0.088 ± 0.038 |
| 4 hrs | 0.032 ± 0.019 | 0.064 ± 0.019 | 0.039 ± 0.014 | 0.087 ± 0.035 |
| 6 hrs | 0.038 ± 0.013 | 0.062 ± 0.021 | 0.043 ± 0.016 | 0.079 ± 0.035 |
| 12 hrs | | 0.048 ± 0.011 | | 0.061 ± 0.027 |
| 18 hrs | | 0.032 ± 0.011 | | 0.045 ± 0.021 |
| 24 hrs | | | | 0.031 ± 0.011 |

Figure 2:
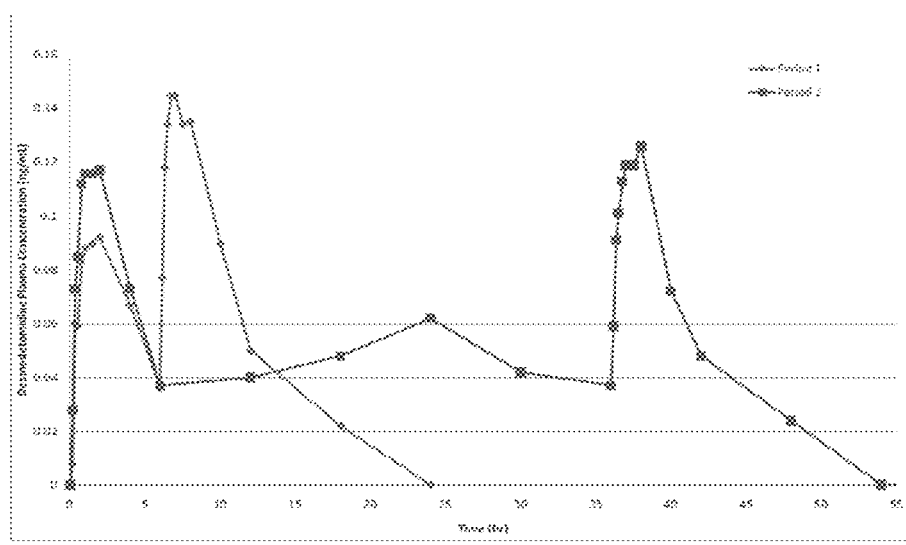
FIG. 2 shows mean dexmedetomidine plasma concentrations (ng/mL) for some embodiments.

These results are illustrated in FIG. 2.

This study supported the safety and tolerability of repeated dosing with intranasal administration. When administered at the six hour dosing interval, there was little evidence of accumulation of dexmedetomidine when comparing the AUC for Dose 1 to Dose 7. DEX-IN.01 was demonstrated to be well tolerated upon repeated dosing with up to seven doses administered on a six hour interval. There was no apparent increase in adverse events, changes in vital signs, or nasal irritation severity with repeated dosing. When administered as an initial 35 µg dose, DEX-IN.01 reached peak plasma concentrations after 1.01-1.26 hours (median) with an average $C_{max}$ of 0.09-0.12 ng/mL. No significant sedation was observed in subjects at various time points during the study.

Example 7: A Randomized, Double-Blind, Placebo-Controlled, Three Period Crossover Evaluation of the Efficacy, Safety, and Pharmacokinetics of Intranasal Dexmedetomidine in Chronic Low Back Pain Subjects A study was performed to evaluate the efficacy, safety, and pharmacokinetics of two dose levels of intranasal dexmedetomidine (DEX-IN.02 and DEX-IN.03) compared with placebo in subjects with chronic low back pain.

Methods: Adult subjects with chronic low back pain symptoms present for greater than three months, and a baseline 24-hour pain intensity≥4 (0-10 scale) were eligible to participate. Subjects were randomly assigned to a treatment sequence with DEX-IN.02 (50 µg; 50 µg/100 µL), DEX-IN.03 (25 µg; 25 µg/50 µL) and matching placebo. Study doses were administered as an intranasal spray using a single dose spray device requiring no priming Doses were administered to a single nostril. Dosing devices were filled with the appropriate volume of drug solution to deliver the designated 25 or 50 µg dose of dexmedetomidine. Study doses were administered on consecutive days, with a minimum 24-hour washout between doses. Subjects with baseline chronic analgesic therapy were allowed to continue their regimen throughout study, but no doses were to be administered within 2 hours of study treatment (unless analgesic rescue was required). Rescue analgesia was available upon subject request according to the individual's baseline pain regimen.

Efficacy assessments included measures of pain intensity (PI), pain relief (PR), and global medication performance (GMP). Efficacy measures were used to calculate the pain intensity difference (PID), summed pain intensity difference (SPID) and total pain relief (TOTPAR) at multiple post-dose time points, and to determine the number of subjects with partial and complete responses to therapy. Safety assessments included collection of vital signs, nasal symptom assessment, sedation, and adverse events. Plasma samples were collected at intervals over the first 12 hours post-dose for pharmacokinetic analysis.

Results:

The study enrolled and treated 24 subjects with DEX-IN.02, DEX-IN.03, and placebo; all enrolled subjects completed all scheduled study doses. Subjects were primarily white (91.7%) and male (58.3%), with a mean age of 33.7±10.19 years. Subjects had primarily visceral pain (91.7%) with a mean history of pain symptoms lasting 6.75±6.85 years. One third of subjects utilized opioid analgesics for their pain symptoms.

Mean improvement in subject PID values were significantly greater for the 50 µg dose (DEX-IN.02) compared with placebo from 45 minutes through 2 hours post-dose (45 min: 2.2 vs. 1.2, p=0.0291; 1 hr: 2.2 vs. 0.8, p=0.0082; 1.5 hr: 2.2 vs. 0.7, p=0.0028; 2 hr: 2 vs. 0.9, p=0.0126). The mean SPID value was significantly greater for the 50 µg dose than placebo at 60 minutes after dose (7.1 vs. 3.6; p=0.0352). Mean TOTPAR was significantly higher for the 50 µg dose than placebo at both 45 and 60 minutes after dose (4.3 vs. 2.5; p=0.0298 and 6.2 vs. 3.3; p=0.0097, respectively). The results for the study are shown in the following tables.

TABLE

Summary of Mean ± SD PID Values for All Post-Dose Time Points

| Time Point | Placebo (N = 24) | DEX-IN.03 (N = 24) | DEX-IN.02 (N = 24) |
|---|---|---|---|
| 10 min | 0.2 ± 0.48 | 0.3 ± 0.53 | 0.5 ± 0.93 |
| 15 min | 0.6 ± 0.93 | 0.7 ± 1.09 | 0.8 ± 1.18 |
| 20 min | 1.0 ± 1.33 | 0.9 ± 1.25 | 1.5 ± 1.32 |
| 30 min | 1.0 ± 1.44 | 1.3 ± 1.36 | 1.9 ± 1.85 |
| 45 min | 1.2 ± 1.63 | 1.4 ± 1.44 | 2.2$^§$ ± 1.72 |
| 60 min | 0.8 ± 1.49 | 1.5 ± 1.47 | 2.2$^¥$ ± 1.82 |
| 90 min | 0.7 ± 1.16 | 1.4 ± 1.41 | 2.2$^¥$ ± 1.81 |
| 2 hours | 0.9 ± 1.28 | 1.3 ± 1.23 | 2.0$^§$ ± 1.76 |
| 4 hours | 1.1 ± 1.75 | 1.5 ± 1.38 | 1.8 ± 1.81 |
| 6 hours | 1.5 ± 1.56 | 1.5 ± 1.10 | 1.6 ± 1.71 |

$^§$ $p < 0.05$;
$^¥$ $p < 0.01$

TABLE

Summary of Mean ± SE SPID Values

| Time Point | Placebo (N = 24) | DEX-IN.03 (N = 24) | DEX-IN.02 (N = 24) |
|---|---|---|---|
| 15 min | 0.6 ± 0.19 | 0.7 ± 0.22 | 0.8 ± 0.24 |
| 30 min | 1.6 ± 0.47 | 1.9 ± 0.48 | 2.7 ± 0.59 |
| 45 min | 2.8 ± 0.78 | 3.3 ± 0.75 | 4.9 ± 0.90 |
| 60 min | 3.6 ± 1.05 | 4.8 ± 1.03 | 7.1* ± 1.24 |

*$p = 0.0352$

TABLE

Summary of Mean ± SE TOTPAR Values

| Time Point | Placebo (N = 24) | DEX-IN.03 (N = 24) | DEX-IN.02 (N = 24) |
|---|---|---|---|
| 15 min | 0.6 ± 0.15 | 0.5 ± 0.15 | 0.8 ± 0.20 |
| 30 min | 1.5 ± 0.35 | 1.3 ± 0.32 | 2.4 ± 0.39 |
| 45 min | 2.5 ± 0.56 | 2.4 ± 0.48 | 4.3$^§$ ± 0.59 |
| 60 min | 3.3 ± 0.74 | 3.5 ± 0.68 | 6.2$^¥$ ± 0.81 |

$^§$ $p < 0.05$;
$^¥$ $p < 0.01$

Mean GMP scores were similar among all 3 treatment groups during both 30- and 60-minute post-dose time points. The 50 ng dexmedetomidine treated group had more subjects with improvement ≥33% and ≥50% at all time points after 15 minutes post dose; 11 DEX-IN.02 treated subjects reported ≥50% improvement at 90 minutes (95% CI, 1.02-7.44) and 10 subjects at 2 hours (95% CI, 1.05-10.63), compared with 4 subjects at 90 minutes and 3 subjects at 2 hours in placebo group. No subjects in any of the treatment groups required rescue medications.

Adverse reactions were generally mild in DEX-IN treated subjects, with 5 events determined to be moderate in severity (2 BP decreased, 1 dizziness, 1 somnolence and 1 hypotension). No SAEs, deaths, or withdrawals due to an AE occurred during the conduct of the study. Changes in systolic and diastolic blood pressure (SBP and DBP respectively) were greater with DEX-IN.02 treated subjects than DEX-IN.03 and placebo treated subjects. Changes in heart rate (HR) were similar following DEX-IN.03 and placebo, while DEX-IN.02 treated subjects had a greater decrease in heart rate; the greatest mean percent change below baseline was −1% for placebo and −9% for DEX-IN.02, while the mean HRs for DEX-IN.03 never decreased below baseline. Results of the nasal assessment of nasal irritation were similar among all treatment groups at all time points with the mean score not exceeding 1 in DEX-IN.02 treated subjects at one hour post-dose (scale of 0-10). Subjects in the DEX-IN.02 treatment group experienced the highest Stanford Sleepiness Scale values 60 minutes post-dose with 17 subjects reporting a score≥5.

A single dose of DEX-IN.03 (25 µg) yielded a mean $C_{max}$ of 0.11 ng/mL with a median $T_{max}$ of 0.75 hrs, while a single dose of DEX-IN.02 (50 µg) yielded a mean $C_{max}$ of 0.25 ng/mL with a median $T_{max}$ of 0.51 hrs. The following tables summarize these results

TABLE

Observed Mean Dexmedetomidine Plasma Concentrations (ng/mL)

| Time Post-Dose | DEX-IN.03 (25 µg) | DEX-IN.02 (50 µg) |
|---|---|---|
| 0 min | 0 | 0 |
| 10 min | 0.047 | 0.098 |
| 15 min | 0.081 | 0.182 |
| 20 min | 0.096 | 0.215 |
| 30 min | 0.111 | 0.212 |
| 45 min | 0.110 | 0.228 |
| 60 min | 0.102 | 0.196 |
| 75 min | 0.094 | 0.183 |
| 90 min | 0.085 | 0.169 |
| 2 hrs | 0.077 | 0.149 |
| 4 hrs | 0.048 | 0.101 |
| 6 hrs | 0.030 | 0.050 |
| 12 hrs | 0 | 0.027 |

TABLE

Observed Pharmacokinetic Properties of Dexmedetomidine

| Parameter | DEX-IN.03 (25 μg) | DEX-IN.02 (50 μg) |
|---|---|---|
| $C_{max}$ (ng/mL) | 0.11 (71.4) | 0.25 (38.3) |
| $T_{max}$ (hrs) | 0.75 (0.25, 4.00) | 0.51 (0.25, 4.00) |
| $AUC_{inf}$ (hr · ng/mL) | 0.48 (13.7) | 0.92 (26.0) |
| $AUC_{0-1}$ (hr · ng/mL) | 0.08 (110.4) | 0.16 (64.1) |
| $AUC_{last}$ (hr · ng/mL) | 0.24 (182.4) | 0.75 (21.6) |
| t½ (hrs) | 2.24 (1.60, 2.45) | 2.05 (1.52, 3.07) |

[1] Geometric means (CV %) for $C_{max}$, $AUC_{0-1}$, $AUC_{last}$ and $AUC_{inf}$; median (min, mix) for $T_{max}$; and arithmetic mean ± SD for $t_{1/2}$ This study shows that the intranasal route is a viable non-invasive means of administering dexmedetomidine. Dosing with DEX-IN.02 and DEX-IN.03 produced more rapid absorption with higher dexmedetomidine peak plasma concentrations than previously explored formulations. Analysis of SPID and TOTPAR values demonstrates the significant analgesic effects of a 50 μg dose of intranasal dexmedetomidine compared with a 25 μg dose or placebo in subjects with CLBP starting 45 minutes post dose. Overall, DEX-IN was well tolerated; the AEs reported were generally mild in severity, while no SAEs were reported.

What is claimed is:

1. A method of treating pain in a human adult in need thereof consisting of intranasally administering to a single nostril a pharmaceutical composition comprising dexmedetomidine, or a pharmaceutically acceptable salt thereof, at a dose of about 35 μg, about 40 μg, about 45 μg, about 50 μg, about 55 μg, or about 60 μg whereby the dexmedetomidine, or pharmaceutically acceptable salt thereof, produces a Cplasma of about 0.1 ng/ml within about 15 minutes to about 20 minutes of administration and has an analgesic effect during the hour immediately after administration of the dexmedetomidine, or pharmaceutically acceptable salt thereof, wherein the human adult is cooperative, oriented, and tranquil during the hour immediately after administration of the dexmedetomidine, or pharmaceutically acceptable salt thereof.

2. The method of claim 1 comprising intranasally spraying in the human the dexmedetomidine, or a pharmaceutically acceptable salt thereof, wherein the spray comprises droplets which have a Dv90 of less than about 150 μm.

3. The method of claim 1 wherein the plasma $C_{max}$ of dexmedetomidine is about 0.08 ng/ml to about 0.2 ng/ml.

4. The method of claim 1 wherein the plasma $C_{max}$ of dexmedetomidine is about 0.15 ng/ml.

5. The method of claim 1 wherein the plasma $C_{max}$ of dexmedetomidine is about 0.2 ng/ml.

6. The method of claim 1 wherein the $T_{max}$ of dexmedetomidine is less than about 1 hour.

7. The method of claim 1 wherein the $T_{max}$ is less than about 50 minutes.

8. The method of claim 1 wherein the dexmedetomidine, or pharmaceutically acceptable salt thereof, is administered as a unit dose of about 40 μg, about 45 μg, about 50 μg, or about 55 μg.

9. The method of claim 1 wherein there is no or minimal effect on blood pressure within the hour immediately after administration of the dexmedetomidine, or pharmaceutically acceptable salt thereof.

10. The method of claim 1 further comprising administering to the human one or more additional therapeutic agents.

11. The method of claim 10 wherein the one or more additional therapeutic agents is chosen from an opioid analgesic, a non-opioid analgesic, a vitamin, a vasodilator, a benzodiazepine, a triptan, an anti-convulsant, an anti-depressant, an anti-nausea medication, and an anti-hypertensive.

12. The method of claim 1 wherein the dexmedetomidine, or pharmaceutically acceptable salt thereof, is administered about every 6 hours.

13. The method of claim 1 wherein the pain is idiopathic pain or is associated with or caused by cancer, viral infection, physical trauma, arthritis, headache, migraine, or lower back pain.

14. The method of claim 13 wherein the idiopathic pain is neuralgia, myalgia, hyperalgia, hyperpathia, neuritis, or neuropathy.

15. The method of claim 1 wherein the dexmedetomidine, or pharmaceutically acceptable salt thereof, is administered intranasally with a metered dose device.

\* \* \* \* \*